(12) United States Patent
Swaney et al.

(10) Patent No.: US 10,548,630 B2
(45) Date of Patent: Feb. 4, 2020

(54) SYSTEM, METHOD, AND APPARATUS FOR CONFIGURATION, DESIGN, AND OPERATION OF AN ACTIVE CANNULA ROBOT

(71) Applicant: Vanderbilt University, Nashville, TN (US)

(72) Inventors: Philip J. Swaney, Nashville, TN (US); Ray Lathrop, Nashville, TN (US); Jessica Burgner, Hannover (DE); Kyle Weaver, Thompson Station, TN (US); Hunter B. Gilbert, Nashville, TN (US); Robert J. Webster, Nashville, TN (US); David B. Comber, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 752 days.

(21) Appl. No.: 14/177,864

(22) Filed: Feb. 11, 2014

(65) Prior Publication Data
US 2015/0223832 A1 Aug. 13, 2015

(51) Int. Cl.
A61B 17/34 (2006.01)

(52) U.S. Cl.
CPC .. *A61B 17/3421* (2013.01); *A61B 2017/3443* (2013.01)

(58) Field of Classification Search
CPC ........ A61B 17/3421; A61B 2017/3409; A61B 34/30; A61B 2034/301; A61B 1/00133;
(Continued)

(56) References Cited

U.S. PATENT DOCUMENTS

2004/0111081 A1* 6/2004 Whitman ........... A61B 10/0233
606/1
2005/0234435 A1* 10/2005 Layer ................. A61B 17/3403
606/1
(Continued)

OTHER PUBLICATIONS

A. H. Gosline, N. V. Vasilyev, A. Veeramani, M. Wu, G. Schmitz, R. Chen, V. Arabagi, P. J. del Nido, and P. E. Dupont,"Metal MEMS tools for beating-heart tissue removal," in Proc. IEEE Int. Conf. Robot. Autom., May 2012, pp. 1921-1926.
(Continued)

*Primary Examiner* — Katherine M Shi
*Assistant Examiner* — Lindsey Bachman
(74) *Attorney, Agent, or Firm* — Tarolli, Sundheim, Covell & Tummino LLP

(57) ABSTRACT

The present invention relates to a system and apparatus for implementing a method for identifying tube parameters of a curved tube of an active cannula for operating on a target in a patient. The method includes the step (a) of acquiring a model of the patient anatomy including the target. The method also includes the step (b) of selecting a set of parameters characterizing a curved tube. The method also includes the step (c) of computing a workspace for an active cannula having the selected curved tube parameters. The method also includes the step (d) of comparing the workspace to the anatomical model to determine the degree to which an active cannula having the selected curved tube parameters covers the target. The method also includes the step (e) of repeating steps (b) through (d) through a defined number of curved tube parameter sets. The method also includes the step (f) of identifying the curved tube parameters that provide an active cannula with an optimal degree of target coverage.

17 Claims, 20 Drawing Sheets

(58) Field of Classification Search
CPC . A61B 17/37; A61B 17/70; A61B 2017/3445; A61M 25/0113
See application file for complete search history.

(56) References Cited

U.S. PATENT DOCUMENTS

| | | | |
|---|---|---|---|
| 2005/0261735 A1* | 11/2005 | Shibata | A61B 10/06 606/205 |
| 2009/0048610 A1* | 2/2009 | Tolkowsky | A61B 90/11 606/130 |
| 2009/0248045 A1 | 10/2009 | Trovato | |
| 2011/0015490 A1 | 1/2011 | Trovato et al. | |
| 2011/0092810 A1 | 4/2011 | Trovato | |
| 2011/0118756 A1* | 5/2011 | Brock | A61B 34/74 606/130 |
| 2011/0166514 A1 | 7/2011 | Trovato et al. | |
| 2011/0201887 A1 | 8/2011 | Greenblatt et al. | |
| 2011/0238083 A1* | 9/2011 | Moll | A61B 8/12 606/130 |
| 2011/0295199 A1 | 12/2011 | Popovic et al. | |
| 2012/0029288 A1 | 2/2012 | Greenblatt et al. | |

OTHER PUBLICATIONS

A. Quinones Hinojosa, M. L. Ware, N. Sanai, and M. W. McDermott, "Assessment of image guided accuracy in a skull model: Comparison of frameless stereotaxy techniques vs. frame-based localization," J. Neurooncol., vol. 76, No. 1, pp. 65-70, 2006.
A. R. Pelton, S. M. Russell, and J. DiCello. The Physical Metallurgy of Nitinol for Medical Applications. JOM, 55(5):33-37, May 2003.
B. Davies, "A review of robotics in surgery," Proceedings of the Institution of Mechanical Engineers, Part H: Journal of Engineering in Medicine, vol. 214, No. 1, pp. 129-140, 2000.
B. Englot and F. Hover. Planning Complex Inspection Tasks Using Redundant Roadmaps. In International Symposium of Robotics Research (ISRR), pp. 1-16, 2011.
Barlas, O., Karadereler, S., Bahar, S., Yesilot, N., Krespi, Y., Solmaz, B., and Bayindir, O., "Image-guided keyhole evacuation of spontaneous supratentorial intracerebral hemorrhage.," Minimally Invasive Neurosurgery 52(2), 62-8(2009).
C. Bedell, J. Lock, A. Gosline, and P. E. Dupont, "Design Optimization of Concentric Tube Robots Based on Task and Anatomical Constraints," in International Conference on Robotics and Automation, 2011, pp. 398-403.
C. C. Chen, D. Y. Cho, C. S. Chang, J. T. Chen, W. Y. Lee, and H. C. Lee, "A stainless steel sheath for endoscopic surgery and its application in surgical evacuation of putaminal haemorrhage." Journal of Clinical Neuroscience, vol. 12, No. 8, pp. 937-940, 2005.
C. H. Chen, H. T. Lee, C. C. Shen, and M. H. Sun, "Aspiration of hypertensive intracerebral hematoma with frameless and fiducial-free navigation system: technical note and preliminary result." Stereotactic and Functional Neurosurgery, vol. 86, No. 5, pp. 288-291, 2008.
C. J. van Asch, et al., "Incidence, case fatality, and functional outcome of intracerebral haemorrhage over time, according to age, sex, and ethnic origin: a systematic review and meta-analysis." Lancet neurology, vol. 9, No. 2, pp. 167-176, 2010.
C. M. Graves, A. Slocum, R. Gupta, and C. J. Walsh, "Towards a compact robotically steerable thermal ablation probe," in Proc. IEEE Int. Conf. Robot. Autom., May 2012, pp. 709-714.
C. M. Miller, P. Vespa, J. L. Saver, C. S. Kidwell, S. T. Carmichael, J. Alger, J. Frazee, S. Starkman, D. Liebeskind, V. Nenov, R. Elashoff, and N. Martin, "Image-guided endoscopic evacuation of spontaneous intracerebral hemorrhage," Surg. Neurol., vol. 69, No. 5, pp. 441-446, 2008.
D. A. Mendelow, et al., "Early surgery versus initial conservative treatment in patients with spontaneous supratentorial intracerebral haematomas in the International Surgical Trial in Intracerebral Haemorrhage (STICH): a randomised trial." Lancet, vol. 365, No. 9457, pp. 387-397.

D. C. Rucker and R. J. Webster III. Computing Jacobians and compliance matrices for externally loaded continuum robots. IEEE International Conference on Robotics and Automation, pp. 945-950, 2011.
D. C. Rucker and R. J. Webster III. Mechanics of bending, torsion, and variable precurvature in multi-tube active cannulas. IEEE International Conference on Robotics and Automation, pp. 2533-2537, 2009.
D. C. Rucker and R. J. Webster III. Mechanics-based modeling of bending and torsion in active cannulas. IEEE RAS/EMBS International Conference on Biomedical Robotics and Biomechatronics, pp. 704-709, 2008.
D. C. Rucker and R. J. Webster III. Parsimonious evaluation of concentric-tube continuum robot equilibrium conformation. IEEE Transactions on Biomedical Engineering, 56(9):2308-2311, 2009.
D. C. Rucker, B. A. Jones, and R. J. Webster III, "A Geometrically Exact Model for Externally Loaded Concentric-Tube Continuum Robots," Transactions on Robotics, vol. 26, No. 5, pp. 769-780, 2010.
D. C. Rucker, B. A. Jones, and R. J. Webster III. A model for concentric tube continuum robots under applied wrenches. IEEE International Conference on Robtics and Automation, pp. 1047-1052, 2010.
D. C. Rucker, J. M. Croom, and R. J. Webster III. Aiming surgical lasers with an active cannula. ASME Journal of Medical Devices, 3(2):027506, 2009.
D. C. Rucker, R. J. Webster III, G. S. Chirikjian, and N. J. Cowan, "Equilibrium Conformations of Concentric-Tube Continuum Robots," International Journal of Robotics Research, vol. 29, No. 10, pp. 1263-1280, 2010.
D. F. Louw, T. Fielding, P. B. McBeth, D. Gregoris, P. Newhook, and G. R. Sutherland, "Surgical robotics: A review and neurosurgical prototype development," Neurosurg., vol. 54, No. 3, pp. 525-536, 2004.
D. W. Newell, M. M. Shah, R. Wilcox, D. R. Hansmann, E. Melnychuk, J. Muschelli, and D. F. Hanley, "Minimally invasive evacuation of spontaneous intracerebral hemorrhage using sonothrombolysis." Journal of Neurosurgery, vol. 115, No. 3, pp. 592-601, 2011.
E. M. Arkin and C. L. Smith. Optimization Problems Related to Zigzag Pocket Machining. In ACM-SIAM Symposium on Discrete Algorithms, pp. 419-428, 1997.
E. M. Arkin, S. P. Fekete, and J. S. Mitchell. Approximation algorithms for lawn mowing and milling. Computational Geometry, 17(1-2):25-50, 2000.
G. Dogangil, B. L. Davies, and F. Rodriguez y Baena, "A review of medical robotics for minimally invasive soft tissue surgery," Proc. Inst. Mech. Eng. Part H: J. Eng. Med., vol. 224, No. 5, pp. 653-679, 2010.
G. Maira, C. Anile, C. Colosimo, and G. F. Rossi, "Surgical treatment of primary supratentorial intracerebral hemorrhage in stuporous and comatose patients." Neurological Research, vol. 24, No. 1, pp. 54-60, 2002.
H. Choset. Coverage for robotics A survey of recent results. Annals of Mathematics and Artificial Intelligence, 31 (1-4):113-126, 2001.
H. Choset. Coverage of Known Spaces : The Boustrophedon Cellular Decomposition. Autonomous Robots, 9(3):247-253, 2000.
H. Su, D. C. Cardona, W. Shang, A. Camilo, G. A. Cole, D. C. Rucker, R. J. Webster, and G. S. Fischer, "A MRI-guided concentric tube continuum robot with piezoelectric actuation: A feasibility study," in International Conference on Robotics and Automation. IEEE, 2012, pp. 1939-1945.
H. Takizawa, K. Sugiura, M. Baba, and J. D. Miller. Analysis of intracerebral hematoma shapes by numerical computer stimulation using the finite element method. Neurologia Medico-Chirurgica, 34:65-69, 1994.
I. Chen, A. M. Coffey, S. Y. Ding, P. Dumpuri, B. M. Dawant, R. C. Thompson, and M. I. Miga. Intraoperative brain shift compensation: Accounting for dural septa. IEEE Transactions on Biomedical Engineering, 58:499-508, 2011.
I. Chen, R. E. Ong, A. L. Simpson, K. Sun, R. C. Thompson, and M. I. Miga. Integrating retraction modeling into an atlas-based

(56) References Cited

OTHER PUBLICATIONS framework for brain shift prediction. IEEE Transactions on Biomedical Engineering, 2013. (In Press).

J. A. Engh, G. Podnar, D. Kondziolka, and C. N. Riviere, "Toward effective needle steering in brain tissue," in Proc. Int. Conf. IEEE Eng. Med. Biol. Soc., Aug./Sep. 2006, vol. 1, pp. 559-562.

J. Burgner, D. C. Rucker, H. B. Gilbert, P. J. Swaney, K. D. Weaver, and R. J. Webster III. A Telerobotic System for Transnasal Surgery. IEEE Transactions on Mechatronics, 2013.

J. Burgner, H. B. Gilbert, and R. J. Webster III, "On the computational design of concentric tube robots: Incorporating volume-based objectives," in Proc. IEEE Int. Conf. Robot. Autom., 2013.

J. Burgner, P. J. Swaney, D. C. Rucker, H. B. Gilbert, S. T. Nill, P. T. Russell, K. D. Weaver, and R. J. Webster III, "A bimanual teleoperated system for endonasal skull base surgery," in International Conference on Intelligent Robots and Systems, 2011, pp. 2517-2523.

J. Burgner, P. J. Swaney, R. A. Lathrop, K. D. Weaver, and R. J. Webster III. Debulking from within: A robotic steerable cannula for intracerebral hemorrhage evacuation. IEEE Transactions on Biomedical Engineering, 2013. (In Press).

J. Burgner, P. J. Swaney, R. A. Lathrop, K. D. Weaver, and R. J. Webster III. Robot-assisted intracerebral hemorrhage evacuation: An experimental evaluation. SPIE Medical Imaging, 2013.

J. Burgner, P. J. Swaney, T. L. Bruns, M. S. Clark, D. C. Rucker, E. C. Burdette, R. J. Webster III, "An autoclavable steerable cannula manual deployment device: Design and accuracy analysis," ASME Journal of Medical Devices, vol. 6, No. 4, p. 041007, Accepted.

J. M. Murthy, G. V. Chowdary, T. V. Murthy, P. S. Bhasha, and T. J. Naryanan, "Decompressive craniectomy with clot evacuation in large hemispheric hypertensive intracerebral hemorrhage," Neurocritical Care, vol. 2, No. 3, pp. 258-262, 2005.

J. M. Simard, "Plenary lectures: Problems in neurosurgery—a rich environment for engineers," in Proc. IEEE Int. Conf. Biomed. Robot. Biomechatron., 2012, p. L. DOI: 10.1109/BioRob.2012.6290953.

J. Zhang, N. Yoganandan, F. A. Pintar, and T. A. Gennarelli. Temporal cavity and pressure distribution in a brain simulant following ballistic penetration. Journal of Neurotrauma, 22(11):1335-1347, 2005.

K. R. Wagner, G. H. Xi, Y. Hua, M. Kleinholz, G. M. deCourtenMyers, R. E. Myers, J. P. Broderick, and T. G. Brott. Lobar intracerebral hemorrhage model in pigs—rapid edema development in perihematomal white matter. Stroke, 27 (3):490-497, 1996.

L. A. Platenik, M. I. Miga, D. W. Roberts, K. E. Lunn, F. E. Kennedy, A. Hartov, and K. D. Paulsen. In vivo quantification of retraction deformation modeling for updated image-guidance during neurosurgery. IEEE Transactions on Biomedical Engineering, 49:823-835, 2002.

L. Elijovich, P. V. Patel, and J. C. Hemphill, "Intracerebral hemorrhage," Seminars in neurology, vol. 28, No. 5, pp. 657-667, 2008.

L. G. Torres, R. J. Webster III, and R. Alterovitz, "Task-oriented design of concentric tube robots using mechanics-based models," International Conference on Intelligent Robots and Systems, 2012.

L. Zamorano, Q. Li, S. Jain, and G. Kaur, "Robotics in neurosurgery: state of the art and future technological challenges." The International Journal of Medical Robotics and Computer Assisted Surgery, vol. 1, No. 1, pp. 7-22, 2004.

M. I. Miga, D. W. Roberts, A. Hartov, S. Eisner, J. Lemery, F. E. Kennedy, and K. D. Paulsen. Updated neuroimaging using intraoperative brain modeling and sparse data. Stereotactic and Functional Neurosurgery, 72:103-106, 1999.

M. I. Miga, D. W. Roberts, F. E. Kennedy, L. A. Platenik, A. Hartov, K. E. Lunn, and K. D. Paulsen. Modeling of retraction and resection for intraoperative updating of images. Neurosurgery, 49:75-84, 2001.

M. I. Miga, K. D. Paulsen, F. E. Kennedy, P. J. Hoopes, A. Hartov, and D. W. Roberts. In vivo analysis of heterogeneous brain deformation computations for model-updated image guidance. Comput Methods Biomech Biomed Engin, 3:129-146, 2000.

M. I. Miga, K. D. Paulsen, J. M. Lemery, S. D. Eisner, A. Hartov, F. E. Kennedy, and D. W. Roberts. Modelupdated image guidance: Initial clinical experiences with gravity-induced brain deformation. IEEE Transactions on Medical Imaging, 18:866-874, 1999.

M. I. Miga, K. D. Paulsen, P. J. Hoopes, F. E. Kennedy, A. Hartov, and D. W. Roberts. In vivo modeling of interstitial pressure in the brain under surgical load using finite elements. Journal of Biomechanical Engineering—Transactions of the ASME, 122:354-363, 2000.

M. I. Miga, K. D. Paulsen, P. J. Hoopes, F. E. Kennedy, A. Hartov, and D.W. Roberts. In vivo quantification of a homogeneous brain deformation model for updating preoperative images during surgery. IEEE Transactions on Biomedical Engineering, 47:266-273, 2000.

M. J. Drexel, G. S. Selvaduray, and A. R. Pelton. The Effects of Cold Work and Heat Treatment on the Properties of Nitinol Wire. In Proceedings of the International Conference on Shape Memory and Superelastic Technologies, pp. 447-454. ASM International, 2006.

M. Mcdonald, N. Konyer, and M. J. Bronskill, "MRI-guided neurosurgery: Accuracy of the navigus trajectory guide," Int. Soc. Magn. Resonace Med. 10, vol. 94, No. 1, p. 2075, 2002.

M. Terayama, J. Furusho, and M. Monden, "Curved multi-tube device for path-error correction in a needle-insertion system." The International Journal of Medical Robotics and Computer Assisted Surgery, vol. 3, No. 2, pp. 125-134, 2007.

M. Waringo, D. Henrich, and U. Bayreuth. 3-Dimensionale schichtweise Bahnplanung fur Any-Time-Frasanwendungen 3-Dimensional Layered Path Planning for Anytime Milling Applications. In Robotik, pp. 781-788, 2004.

Mendelow, A.D., Gregson, B.A., Fernandes, H.M., Murray, G.D., Teasdale, G.M., Hope, D.T., Karimi, A., Shaw, M.D.M., and Barer, D.H., "Early surgery versus initial conservative treatment in patients with spontaneous supratentorial intracerebral haematomas in the International Surgical Trial in Intracerebral Haemorrhage (STICH): a randomised trial.," Lancet 365(9457), 387-397 (2005).

N. Etminan, K. Beseoglu, B. Turowski, H. J. Steiger, and D. Hanggi, "Perfusion CT in patients with spontaneous lobar intracerebral hemorrhage: Effect of surgery on perihemorrhagic perfusion," Stroke, vol. 43, No. 3, pp. 759-763, 2012.

P. Dumpuri, R. C. Thompson, A. Z. Cao, S. Y. Ding, I. Garg, B. M. Dawant, and M. I. Miga. A fast and efficient method to compensate for brain shift for tumor resection therapies measured between preoperative and postoperative tomograms. IEEE Transactions on Biomedical Engineering, 57:1285-1296, 2010.

P. Dumpuri, R. C. Thompson, B. M. Dawant, A. Cao, and M. I. Miga. An atlas-based method to compensate for brain shift: Preliminary results. Medical Image Analysis, 11:128-145, 2007.

P. E. Dupont, J. Lock, B. Itkowitz, and E. Butler, "Design and Control of Concentric-Tube Robots," Transaction on Robotics, vol. 26, No. 2, pp. 209-225, 2010.

P. J. Swaney, J. Burgner, R. A. Lathrop, H. B. Gilbert, K. D. Weaver, and R. J. Webster III, "Minimally-invasive intracerebral hemorrhage removal using an active cannula," in Proc. IEEE Int. Conf. Robot. Autom., 2013.

P. N. Kongkham, et al., "Complications in 622 cases of frame-based stereotactic biopsy, a decreasing procedure." The Canadian Journal of Neurological Sciences, vol. 35, No. 1, pp. 79-84, 2008.

P. Schiavone, F. Chassat, T. Boudou, E. Promayon, F. Valdivia, and Y. Payan. In vivo measurement of human brain elasticity using a light aspiration device. Medical Image Analysis, 13:673-678, 2009.

P. Stolka and D. Henrich. Improving Navigation Precision of Milling Operations in Surgical Robotics. In IEEE/RSJ International Conference on Intelligent Robots and Systems, pp. 2351-2357, 2006.

R. A. Kaya, O. Turkmenoglu, I. M. Ziyal, T. Dalkilic,, Y. Sahin, and Y. Aydin, "The effects on prognosis of surgical treatment of hypertensive putaminal hematomas through transsylvian transinsular approach." Surgical Neurology, vol. 59, No. 3, pp. 176-183, 2003.

R. H. Taylor, "A perspective on medical robotics," IEEE Proceedings, vol. 94, pp. 1652-1664, 2006.

R. J. Webster III, J. S. Kim, N. J. Cowan, G. S. Chirikjian, and A. M. Okamura, "Nonholonomic modeling of needle steering," Int. J. Robot. Res., vol. 25, No. 5-6, pp. 509-526, 2006.

(56) References Cited

OTHER PUBLICATIONS

R J. Webster III and B. A. Jones, "Design and kinematic modeling of constant curvature continuum robots: A review," Int. J. Robot. Res., vol. 29, No. 13, pp. 1661-1683, 2010.

R. J. Webster III, A. M. Okamura, and N. J. Cowan. Toward active cannulas: Miniature snake-like surgical robots. In Proc. IEEE/RSJ Int. Conf. Intelligent Robots and Systems (IROS), pp. 2857-2863, 2006.

R. J. Webster III, J. M. Romano, and N. J. Cowan. Kinematics and calibration of active cannulas. IEEE International Conference on Robotics and Automation, pp. 3888-3895, 2008.

R. J. Webster III, J. M. Romano, and N. J. Cowan. Mechanics of precurved-tube continuum robots. IEEE Transactions on Robotics, 25(1):67-78, 2009.

R. J. Webster III, J. P. Swensen, J. M. Romano, and N. J. Cowan. Closed-form differential kinematics for concentric-tube continuum robots with application to visual servoing. Springer Tracts in Advanced Robotics, 54:485-494, 2009.

S. H. Tan, P. Y. Ng, T. T. Yeo, S. H. Wong, P. L. Ong, and N. Venketasubramanian, "Hypertensive basal ganglia hemorrhage: A prospective study comparing surgical and nonsurgical management," Surg. Neurol., vol. 56, No. 5, pp. 287-292, 2001.

T. Anor, J. R. Madsen, and P. Dupont, "Algorithms for Design of Continuum Robots Using the Concentric Tubes Approach: A Neurosurgical Example." International Conference on Robotics and Automation, pp. 667-673, 2011.

T. M. Goradia, R. H. Taylor, and L. M. Auer, "Robot-assisted minimally invasive neurosurgical procedures: First experimental experience," in First Joint Conf. Vision, Virtual Reality, Robotics Med. Med. Robot. Comput.Assisted Surgery, 1997, pp. 319-322.

V. L. Roger, et al., "Heart disease and stroke statistics—2011 update: a report from the American Heart Association." vol. 123, No. 4, pp. e18-e209, 2011.

Y. Altshuler and A. M. Bruckstein. Static and expanding grid coverage with ant robots: Complexity results. Theoretical Computer Science, 412(35):4661-4674, Aug. 2011.

Y. Gabriely and E. Rimon. Competitive on-line coverage of grid environments by a mobile robot. Computational Geometry, 24(3):197-224, Apr. 2003.

Y. Gabriely and E. Rimon. Spanning-tree based coverage of continuous areas by a mobile robot. Annals of Mathematics and Artificial Intelligence, 31(1-4):77-98, 2001.

Y. S. Kwoh, J. Hou, E. A. Jonckheere, and S. Hayati, "A robot with improved absolute positioning accuracy for CT guided stereotactic brain surgery," IEEE Trans. Biomed. Eng., vol. 35, No. 2, pp. 153-160, Feb. 1988.

Y. Zuo, G. Cheng, D.-K. Gao, X. Zhang, H.-N. Zhen, W. Zhang, and S.-C. Xiao, "Gross-total hematoma removal of hypertensive basal ganglia hemorrhages: A long-term follow-up," J. Neurol. Sci., vol. 287, No. 1-2, pp. 100-104, 2009.

Z.-J. Chen, G. T. Gillies, W. C. Broaddus, S.S. Prabhu, H. Fillmore, R. M. Mitchell, F.D. Corwin, and P.P. Fatouros, A realistic brain tissue phantom for intraparenchymal infusion studies. Journal of Neurosurgery, 101 (2):31422, 2004.

C. Walsh, J. Franklin, A.H. Slocum, R. Gupta, Characterizaion of Precurved Needles for Use in Distal Tip Manipulation Mechanisms, J. Med. Devices, vol. 4, 2010, 1 page.

\* cited by examiner

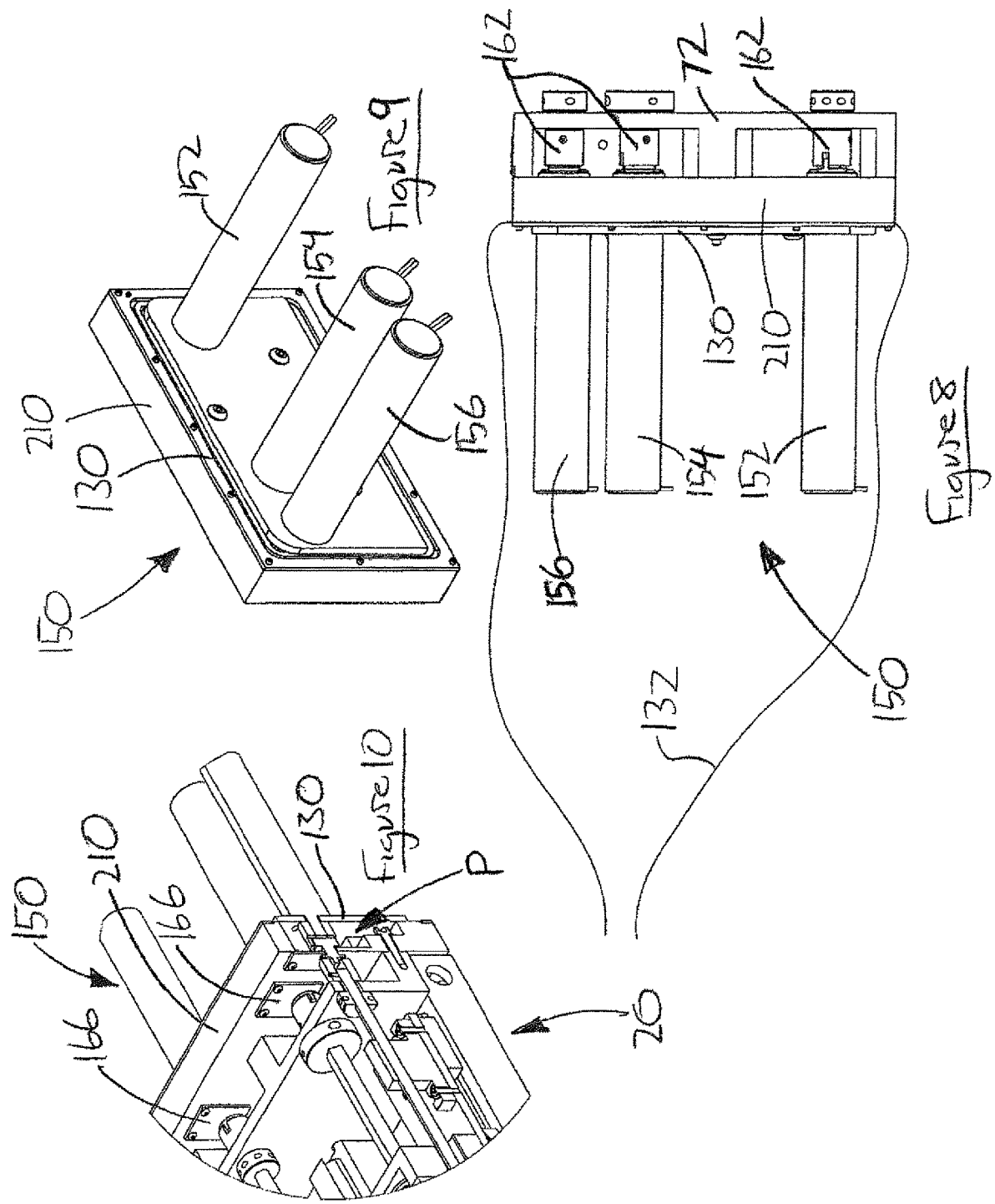

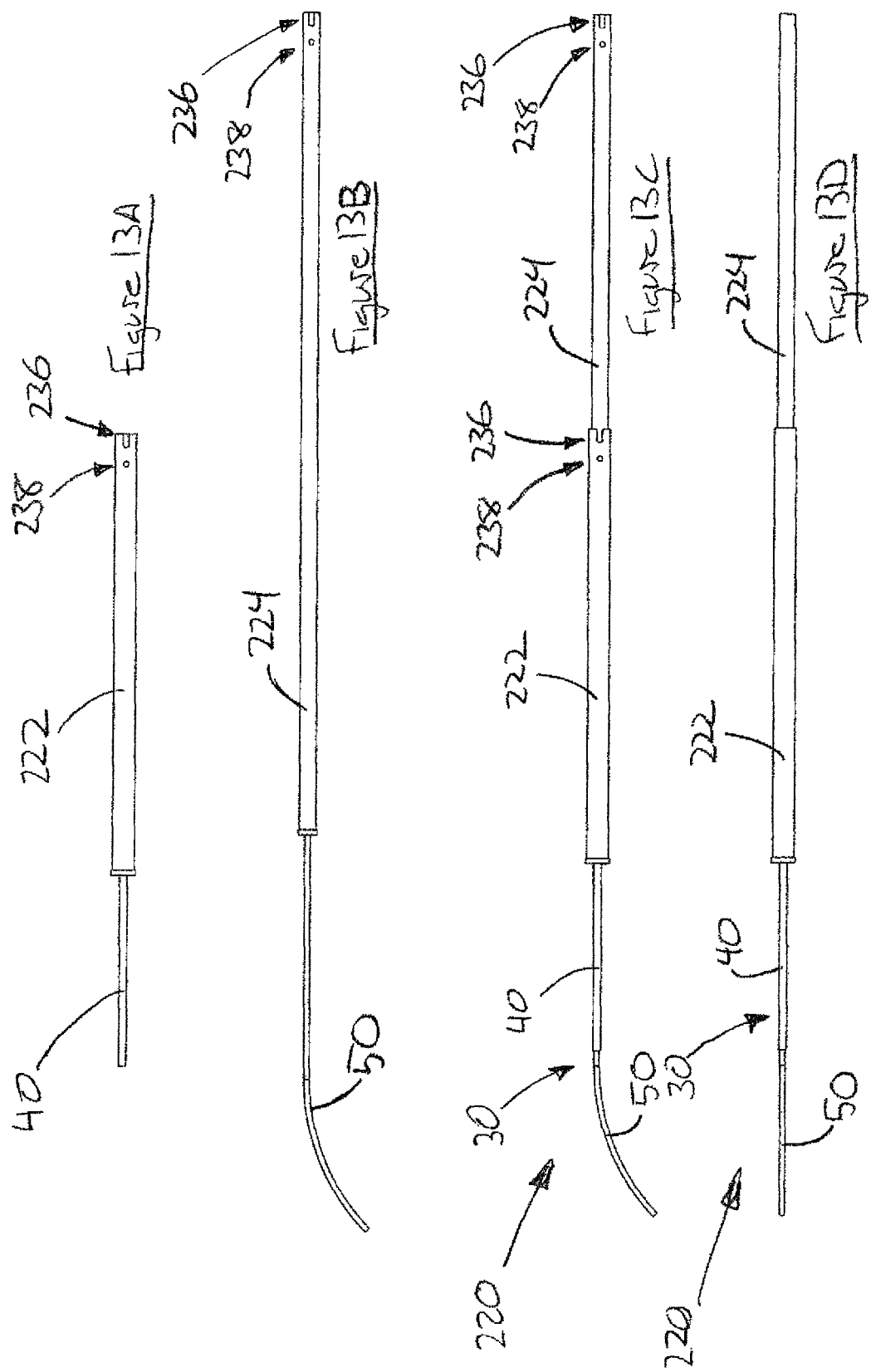

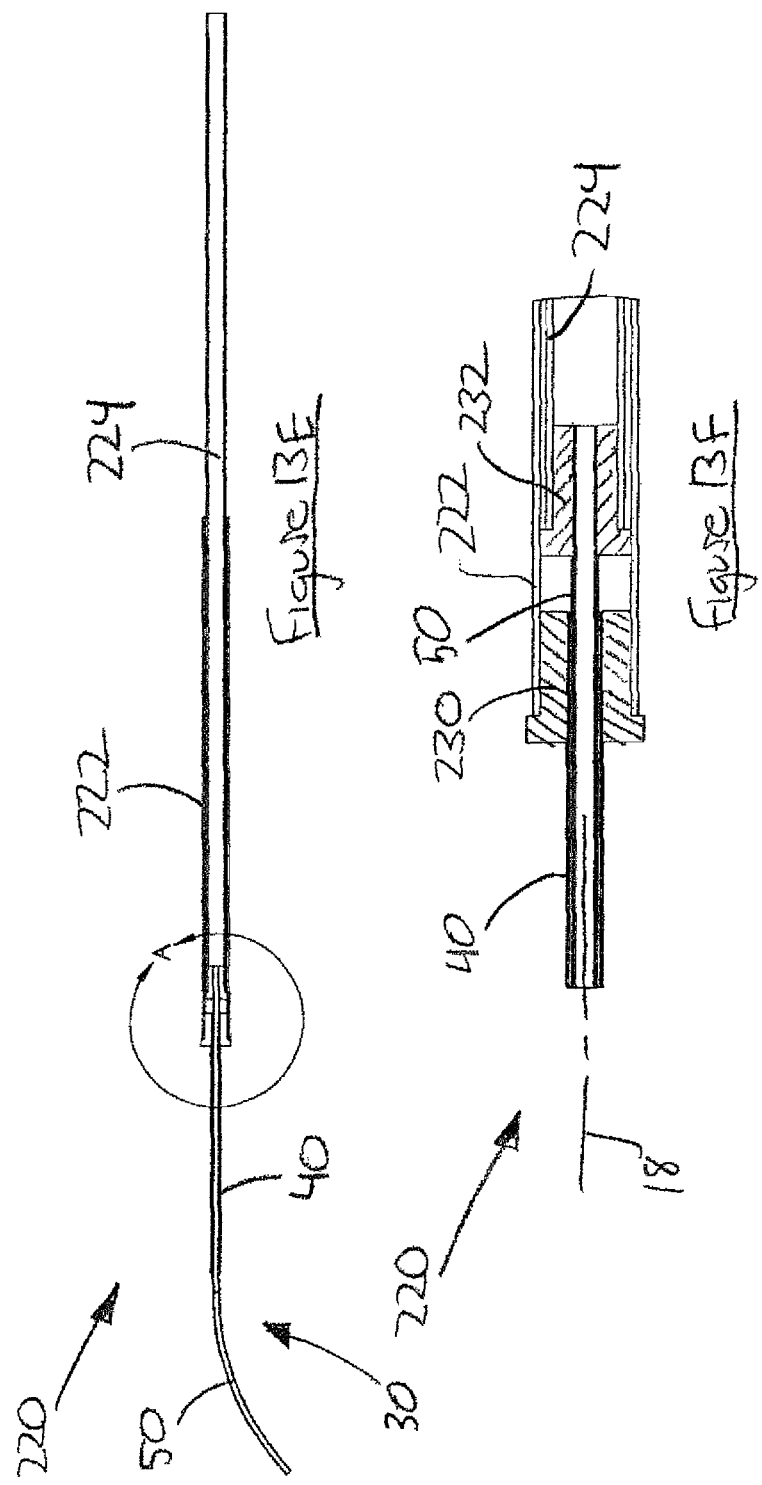

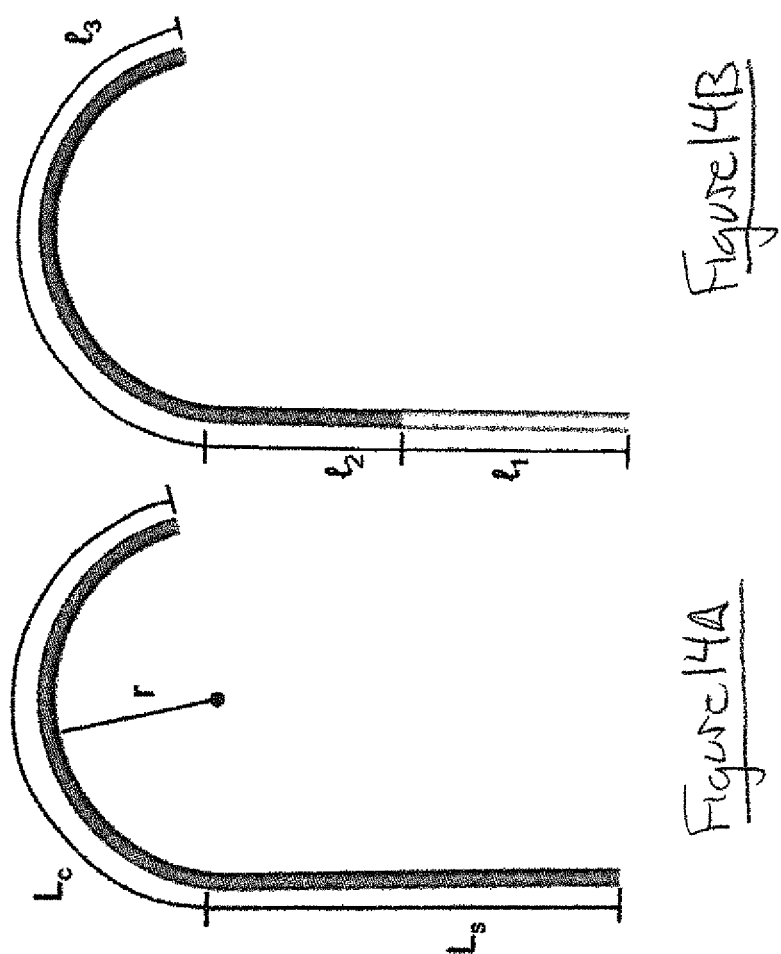

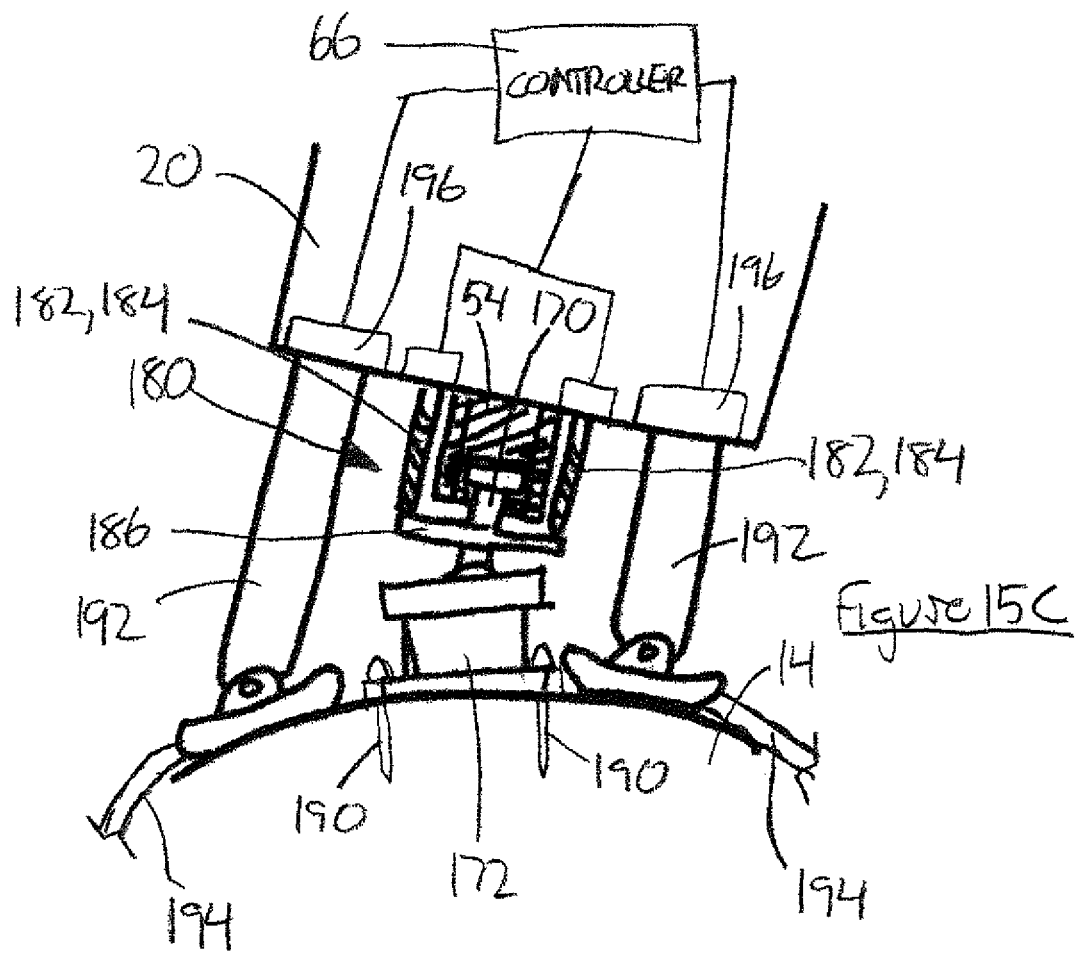

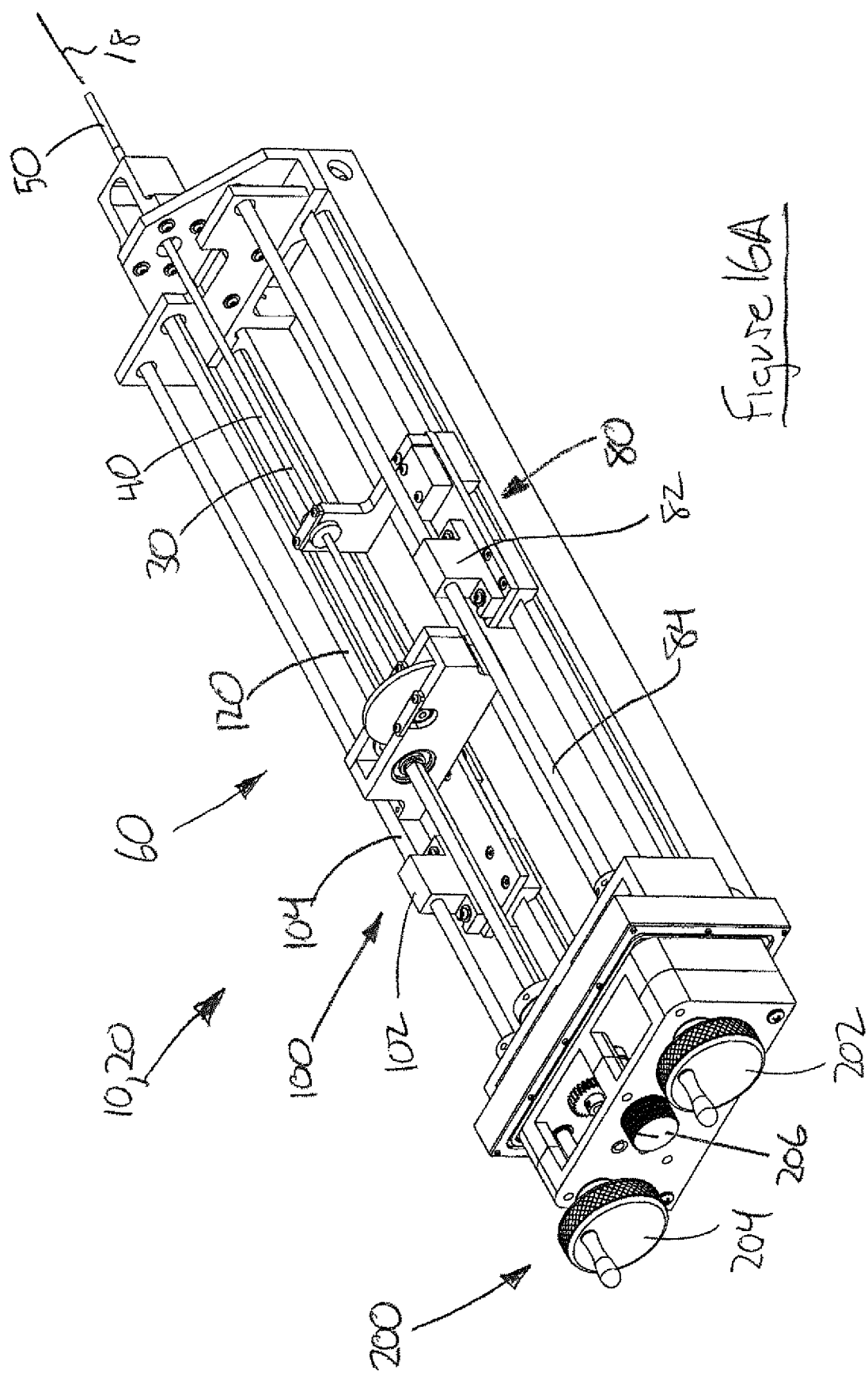

SYSTEM, METHOD, AND APPARATUS FOR CONFIGURATION, DESIGN, AND OPERATION OF AN ACTIVE CANNULA ROBOT

GOVERNMENT FUNDING

This invention was made with government support under grant number IIS1054331 awarded by the National Science Foundation. The government has certain rights in the invention.

FIELD OF THE INVENTION

The invention relates to active cannula robots. More particularly, the invention relates to a system, method, and apparatus for configuring, designing, and operating an active cannula robot to perform a surgical operation. According to one aspect, for an active cannula robot has a straight outer tube and a retractable, curved inner tube, the system performs a method for designing and configuring the curved tube based on the target of the surgical operation. In one particular aspect, the surgical operation is the image guided evacuation of a hematoma resulting from an intracerebral hemorrhage.

BACKGROUND

Minimally invasive surgical techniques are less invasive than open surgery techniques used for the same purpose and are therefore desirable due to their offering reduced trauma, reduced pain & scarring, more rapid recovery, and reduced post-surgical complications. Some of these techniques can be performed robotically. In neurosurgery, attempts have been made at a needle-based minimally invasive robotic approach to treating some conditions. These systems are generally stereotactic robotic systems that use straight needle trajectories with image guidance to hit specific targets at a specific worksite within the brain, in a manner similar to that of a standard brain biopsy. This needle-based approach results in less damage to the surrounding brain tissue during delivery, at the expense of offering no appreciable dexterity once the target is reached. One particular condition that would benefit to a needle based approach that offers dexterity at the worksite is an intracerebral hemorrhage.

Approximately 1 in 50 people will have an intracerebral hemorrhage (ICH) at some point in their lives, and the one-month mortality rate is approximately 40%. ICH occurs when a blood vessel in the brain ruptures and a collection of blood, referred to herein as a "clot" or "hematoma," accumulates within the cranial cavity and compresses the brain. The clot can be treated with drugs or surgical evacuation via open craniotomy to help remove the clot and decompress the brain. While one would expect decompression via clot removal to result in improved patient outcomes, there is no clinical data supporting this for the majority of ICH patients. Benefits of various treatments have only been shown in select patients with small, superficial lesions and a good preoperative performance status. There remains no treatment of proven clinical benefit for typical ICH patients. In standard open surgical procedures, the brain substance is cut with electrocautery and tubular retraction systems, with or without endoscopic assistance, and Archimedes screw-type devices are applied to remove the clot. These current ICH treatments, however, provide only minimal improvement in outcomes.

Some of the ineffectiveness of the current ICH treatments can be attributed to permanent brain injury that is caused by the hemorrhage and is irreversible even with clot removal. Neurosurgeons, however, generally believe that there is a volume of at-risk brain tissue that can be salvaged and returned to pre-injury function if its condition is optimized through decompression. The ability to restore brain tissue to pre-injury function does not necessarily depend on complete removal of the clot. For example, by some estimates, clinically meaningful decompression can begin when approximately 25-50% of the clot is removed.

Decompression through removal of the clot resulting from the ICH, referred to herein as "evacuation" or "debulking," is known to help optimize the condition of the brain. Decompression, however, can be challenging for certain clot locations and shapes, particularly those resulting from deep hemorrhages. For many clots, an operative trajectory of any significant dimension would result in a volume of tissue disruption that is greater than that which would be saved by its evacuation. As a result, only superficial clots are candidates for evacuation using current operative approaches.

SUMMARY

The present invention relates to a robotic active cannula, or active cannula robot, comprising robotically actuated concentric tubes. According to one aspect, the concentric tubes include a straight outer tube that can be actuated for translational movement along an axis and an inner tube that can be actuated for rotation about the axis relative to the outer tube and for insertion from and retraction into the outer tube. The inner tube has an elastic curved end portion that can be retracted into the outer tube. Through extension, retraction, and rotation relative to the outer tube, the end portion of the inner tube can be articulated throughout a workspace that is defined by the curved configuration of the inner tube.

According to another aspect, the active cannula robot is configured to be customized by incorporating multiple inner tubes with various curvatures and/or stiffnesses selected on the basis of the desired workspace. For instance, the curvatures and/or stiffnesses of one or more inner tubes can be selected to treat a surgical target at a known worksite location and having a known shape and extent determined by scanned image data. These multiple inner cannulas can be hot-swapped during the surgical procedure while the outer tube remains in-situ at the worksite. According to this aspect of the invention, the hot-swappable configuration of the inner tubes can allow the aggregate workspace of the active cannula to cover the target at the worksite through the implementation of what amounts to multiple concentric tube robots, used sequentially.

According to this aspect, a kinematic model for the inner tube is evaluated to determine the workspace of a tube having a given set or parameters. The determined workspace is then compared to the scanned image data of the target to determine the extent to which the tube can cover the target. In making this determination, the location and orientation of the target, i.e., the trajectory at which the inner tube accesses the target, is taken into account. This process is repeated through a discrete set of tube parameters, and the tube configuration that offers the optimal workspace for covering the target is selected for the surgical procedure. Through this process, it may be determined that more than one tube, used in succession, can offer an aggregate workspace that is optimally tailored to the target.

One particular neurosurgical operation to which the present invention is particularly well-suited relates to the treatment of an ICH. Thus, according to this aspect, the active cannula robot of the invention can be a 3 degree-of-freedom (DOF) concentric tube robot that can be used to perform image-guided evacuation of clots resulting from an ICH. The robotic system incorporating the robotic active cannula is no more invasive than a standard brain biopsy, yet enables ICH clots to be evacuated via articulation of the curved tip. To perform the evacuation, the inner tube can be configured as an aspiration cannula. The robotic system can thus provide a straight needle trajectory to enter the brain and access the location of the clot in combination with an articulated robotic cannula that can maneuver within the clot at the site of the ICH. According to this aspect, the system can be used to select the inner tube(s) of the active cannula robot so that the robot workspace conforms to the location, shape, and orientation of the ICH clot, as determined from scanned image data.

The present invention relates to a method for identifying tube parameters of a curved tube of an active cannula for operating on a target in a patient. The method includes the step (a) of acquiring a model of the patient anatomy including the target. The method also includes the step (b) of selecting a set of parameters characterizing a curved tube. The method also includes the step (c) of computing a workspace for an active cannula having the selected curved tube parameters. The method also includes the step (d) of comparing the workspace to the anatomical model to determine the degree to which an active cannula having the selected curved tube parameters covers the target. The method also includes the step (e) of repeating steps (b) through (d) through a defined number of curved tube parameter sets. The method also includes the step (f) of identifying the curved tube parameters that provide an active cannula with an optimal degree of target coverage.

According to one aspect of the invention, the step (c) of computing a workspace includes the step of mapping the joint space parameters of the active cannula to configuration space parameters in order to define a forward kinematic model for the active cannula. The step (c) also includes the step of discretizing the joint space of the active cannula to produce a discrete set of joint positions of the active cannula. The step (c) includes the further step of solving the kinematic model for each discrete combination of joint positions to compute the workspace of the active cannula.

According to another aspect of the invention, the step (d) of comparing the computed workspace to the clot model comprises the step of converting the target model to a discrete set of voxels. The step (d) also includes the step of computing a tip position for each of the joint positions of the active cannula. The step (d) includes the further step of evaluating each computed cannula tip position to determine whether it lies within a voxel of the target model. According to another aspect of the invention, the step (d) of comparing the workspace to the model can include determining the degree to which the workspace overlaps the model. According to another aspect of the invention, the method can include the further steps of determining for each joint position whether the entire curve of the active cannula is positioned within the target model, and discarding joint positions combinations in which any portion of the curve is positioned outside the target model.

According to another aspect of the invention, the target can include a clot resulting from an intracerebral hemorrhage in a patient, wherein the step (a) of acquiring a model of the target comprises acquiring a model of the clot mapped relative to a model of the patient's skull. The step of comparing the workspace to the model can include the steps of determining a trajectory at which to access the clot through the patient's skull, and orienting the computed workspace within the clot according to the determined trajectory.

According to another aspect of the invention, the defined number of curved tube parameter sets can be actual parameter sets for cannula tubes in a pre-existing set of tubes, and the active cannula identified in step (f) is one selected from the pre-existing set of tubes.

According to another aspect of the invention, the defined number of curved tube parameter sets can also be theoretical parameter sets that are incremented sequentially through a predetermined range of discrete values, and the curved tube parameters identified in step (f) are for subsequently constructing and configuring a curved tube of the active cannula.

The present invention also relates to an active cannula robot system for performing a surgical treatment on a target in a patient. The system includes an active cannula robot including an outer tube and an inner tube that extends coaxially within the outer tube. The inner tube has a distal curved end portion terminating at a tip. The robot is operable to cause translational movement of the outer and inner tubes along the axis and to cause rotational movement of the inner tube about the axis relative to the outer tube to apply the treatment to the target. A controller is configured to select a configuration of the curved end portion of the tube based on image data related to the target so that the tip can reach at least a threshold portion of the target through the translational and rotational movement.

According to one aspect, the target comprises a clot resulting from an intracerebral hemorrhage. The image data related to the clot is mapped to image data related to the patient's skull so that the position and orientation of the clot in the skull is known. The controller is configured to select the configuration of the curved end portion of the tube on the basis of the image data related to the clot. The controller is configured to select the configuration of the curved end portion of the tube on the further basis of a surgical robot entry point on the patient's skull. According to another aspect, the system includes a trajectory stem and an image guidance system operative to align the trajectory stem along a predetermined trajectory into the patient's brain. The controller is configured to select the configuration of the curved end portion of the tube on the further basis of the trajectory. The image data related to the clot and the image data related to the patient's skull can be CT image data.

According to another aspect, the robot is operable to retract the inner tube into the outer tube, the inner tube being constructed so that the curved end portion when extended from within the outer tube after being retracted within the outer tube resumes its curved configuration. The robot is operable to deliver the active cannula to the target in an axial direction with the inner tube retracted into the outer tube, the robot thereafter extending the curved end portion of the inner tube from the outer tube into the target to treat the target. An aspirator can be operatively connected to the inner tube. The aspirator is operable to apply suction via the inner tube to evacuate the clot.

According to another aspect, the controller can be operable manually to control movement of the active cannula in combination with image guidance to move the tip of the inner tube within the target. The controller can be operable automatically though open loop control to control movement of the active cannula to move the tip of the inner tube within the target. The robot can include a manual actuator including a first manual actuator operable to cause translational movement of the outer tube along the axis, a second manual actuator operable to cause translational movement of the inner tube along the axis, and a third manual actuator operable to impart rotation of the inner tube about the axis.

The present invention also relates to an active cannula robot for performing a surgical operation on a patient. The robot includes an outer tube and an inner tube that extends coaxially with the outer tube. The inner tube includes a curved end portion that is retractable into the outer tube, the curved end portion deforming elastically and conforming to the straight configuration of the outer tube when retracted into the outer tube. The robot is actuatable to cause extension and retraction of the outer tube along the axis. The robot is further actuatable to cause extension of the inner tube from the outer tube, retraction of the inner tube into the outer tube, and rotation of the inner tube relative to the outer tube. A retainer for securing the inner tube to the robot is manually releasable to permit removal and replacement of the inner tube during a surgical operation without retracting the outer tube.

According to one aspect, the robot includes a frame having a front end and an opposite rear end. An outer tube carrier is coupled to the frame. The outer tube carrier is movable along the frame to cause the translational movement of the outer tube along the axis. An inner tube carrier is coupled to the frame. The inner tube carrier is movable along the frame to cause translational movement of the inner tube along the axis. The inner tube carrier includes a tube mount for supporting the inner tube for rotation about the axis. The retainer secures the inner tube in the tube mount. A motor assembly is coupled to the rear end of the frame. The motor assembly includes a first motor operable to move the outer tube carrier along the frame, a second motor operable to move the inner tube carrier along the frame, and a third motor operable to impart rotation of the inner tube about the axis. The retainer permits removal and replacement of the inner tube without disturbing the remaining components of the robot. The outer tube carrier includes emergency release mechanisms that are manually operable to decouple the outer tube carrier from the first motor and to decouple the inner tube carrier from the second motor to permit the tube carriers to be moved manually along the frame in order to retract the inner and outer tubes.

According to one aspect, a trajectory stem guides the outer tube along a predetermined trajectory. A base coupled to the trajectory stem includes a locking mechanism for fixing the position of the trajectory stem at a desired orientation relative to the patient. The base is to the patient. The front end of the frame is configured to be coupled with the trajectory stem that is secured to the patient so that the trajectory stem guides the trajectory of the outer tube when extended from the frame into a patient.

According to another aspect, the outer tube carrier includes a driver block through which a shaft rotatable by the first motor extends. Rotation of the shaft acts on the driver block to impart movement of the outer tube carrier along the frame. The driver block includes an emergency release mechanism that is manually operable to decouple the driver block from the outer tube carrier and thereby decouple the outer tube carrier from the first motor. The inner tube carrier comprises a driver block through which a shaft rotatable by the second motor extends. Rotation of the shaft acts on the driver block to impart movement of the inner tube carrier along the frame. The driver block includes comprising an emergency release mechanism that is manually operable to decouple the driver block from the inner tube carrier and thereby decouple the inner tube carrier from the second motor.

According to another aspect, the motors of the motor assembly are operable to actuate the inner and outer tubes to perform a surgical operation to evacuate a clot resulting from an intracerebral hemorrhage through the inner tube. The first motor is operable to deliver the outer tube to the clot in an axial direction with the inner tube retracted into the outer tube. The second motor is operable to extend the curved end portion of the inner tube from the outer tube into the clot to evacuate the clot. The second and third motors are operable to translate and rotate the curved end portion of the inner tube within the clot to evacuate the clot. The second and third motors are operable to move the position the tip thorough a predetermined path within the clot to evacuate the clot. An aspirator is operatively connected to the inner tube and is operable to apply suction via the inner tube to evacuate the clot.

According to another aspect, a second retainer secures the outer tube to the robot. The second retainer is manually releasable to permit removal and replacement of the outer tube during the surgical operation. The second retainer is manually releasable to permit removal and replacement of the outer tube without disturbing the remaining components of the robot.

According to another aspect, a transmission tube assembly includes concentric transmission tubes arranged coaxially with the inner and outer tubes and configured to transmit at least one of translational and rotational movement from an actuator assembly to the inner and outer tubes.

According to another aspect, a transmission tube assembly includes an outer transmission tube and an inner transmission tube that extend coaxially with each other and with the outer and inner tubes. The outer transmission tube is coupled to the outer tube and the inner transmission tube is coupled to the inner tube. The robot is actuatable to cause extension and retraction of the outer transmission tube along the axis. The robot is also actuatable to cause extension of the inner transmission tube from the outer transmission tube, retraction of the inner transmission tube into the outer tube, and rotation of the of the inner tube relative to the outer transmission tube, the extension, retraction, and rotation of the inner and outer transmission tubes producing corresponding movements of the inner and outer tubes. The tubes of the transmission tube assembly have torsional stiffnesses that are greater than torsional stiffnesses of the outer and inner tubes.

According to another aspect, the robot includes a frame having a front end and an opposite rear end. An outer tube carrier is coupled to the frame, the outer tube carrier is movable along the frame to cause the translational movement of the outer tube along the axis. An inner tube carrier is coupled to the frame. The inner tube carrier is movable along the frame to cause translational movement of the inner tube along the axis. The inner tube carrier includes a tube mount for supporting the inner tube for rotation about the axis. The retainer secures the inner tube in the tube mount. A manual actuator is coupled to the rear end of the frame. The manual actuator includes a first manual actuator operable to move the outer tube carrier along the frame, a second manual actuator operable to move the inner tube carrier along the frame, and a third manual actuator operable to impart rotation of the inner tube about the axis.

According to another aspect, an active cannula robot for performing a surgical operation on a patient. The robot includes an active cannula comprising an outer tube and an inner tube that extends coaxially within the outer tube. A frame supports the active cannula. An actuator actuates the active cannula to cause translational movement of the outer and inner tubes along the axis. An emergency release mechanism is manually operable to decouple the outer and inner tubes from the actuator to permit manual retraction of the tubes.

According to a further aspect, an active cannula robot for performing a surgical operation on a patient includes an active cannula comprising an outer tube and an inner tube that extends coaxially within the outer tube. A frame supports the active cannula. An actuator actuates the active cannula to cause translational movement of the outer and inner tubes along the axis. A retainer is manually operable to permit swapping inner tubes during the surgical operation without disturbing the remaining components of the robot.

DRAWINGS

The invention may be best understood by reference to the following description taken in conjunction with the accompanying drawing figures in which:

FIGS. 8-10 are detail views illustrating a sterilization feature of the active cannula robot.

FIGS. 13A-13F illustrate a torque transmitting feature of the active cannula robot.

FIGS. 14A and 14B are schematic illustrations that depict certain parameters of the active cannula robot.

FIGS. 15A-15C are schematic illustrations that depict an alignment feature of the active cannula robot system.

FIGS. 16A and 16B illustrate an embodiment of the active cannula robot system incorporating manual controls.

DESCRIPTION

The invention relates generally to concentric tube robots. According to one aspect, the invention relates to a system, method, and apparatus for configuring, designing, and operating an active cannula robot to perform a surgical operation. The active cannula robot has a straight outer tube and a retractable, curved inner tube. The system is operable to perform a robotic surgical operation on a target at a work site in a patient. The system is also operable to design and configure the curved inner tube of the robot to have a workspace tailored to the target of the surgical operation based on scanned image data related to the target. In one particular implementation of the invention, the system designs and configures the robot to have a workspace tailored to the shape, location, and orientation of an ICH clot, and operates the robot to perform the image guided evacuation of the ICH clot.

Through the invention, an active cannula configuration that provides optimal coverage for a particular target, such as an ICH clot, can be identified and implemented. By "optimal," it is meant to describe the identification of the configuration that is best-suited under the given circumstances to provide the required therapy. Thus, the optimal configuration may not necessarily be the one that provides the best coverage of the target. Other factors, such as patient risk can affect the determination of what is "optimal" under the circumstances. For example, a neurosurgeon may determine that a configuration that covers the largest portion of a target may pose too large a risk to warrant its use and therefore could opt for a different configuration that lessens the risk but that also reduces coverage of the target. In the ICH clot removal scenario, choosing a configuration that may not cover the largest possible area of the clot not in order to reduce the risk of damaging adjacent brain tissue could nonetheless be considered the optimal configuration.

The active cannula robot system of the invention can be used to perform a wide variety of surgical operations on a target at a worksite in a patient. Therefore, any characterization of the robot herein as an ICH clot evacuation robot is not meant to be limiting, but instead merely illustrative of one particular implementation selected from the wide variety of implementations to which the system is applicable. In this description, the term "clot" is used to refer to the collection of blood resulting from an ICH, which can also be referred to interchangeably as a "hematoma." Also, in this description, the term "debulking" is used to refer to the removal of the clot, which can also be referred to interchangeably as "evacuating" the clot.

Concentric Tube Robot System

Figure 1:
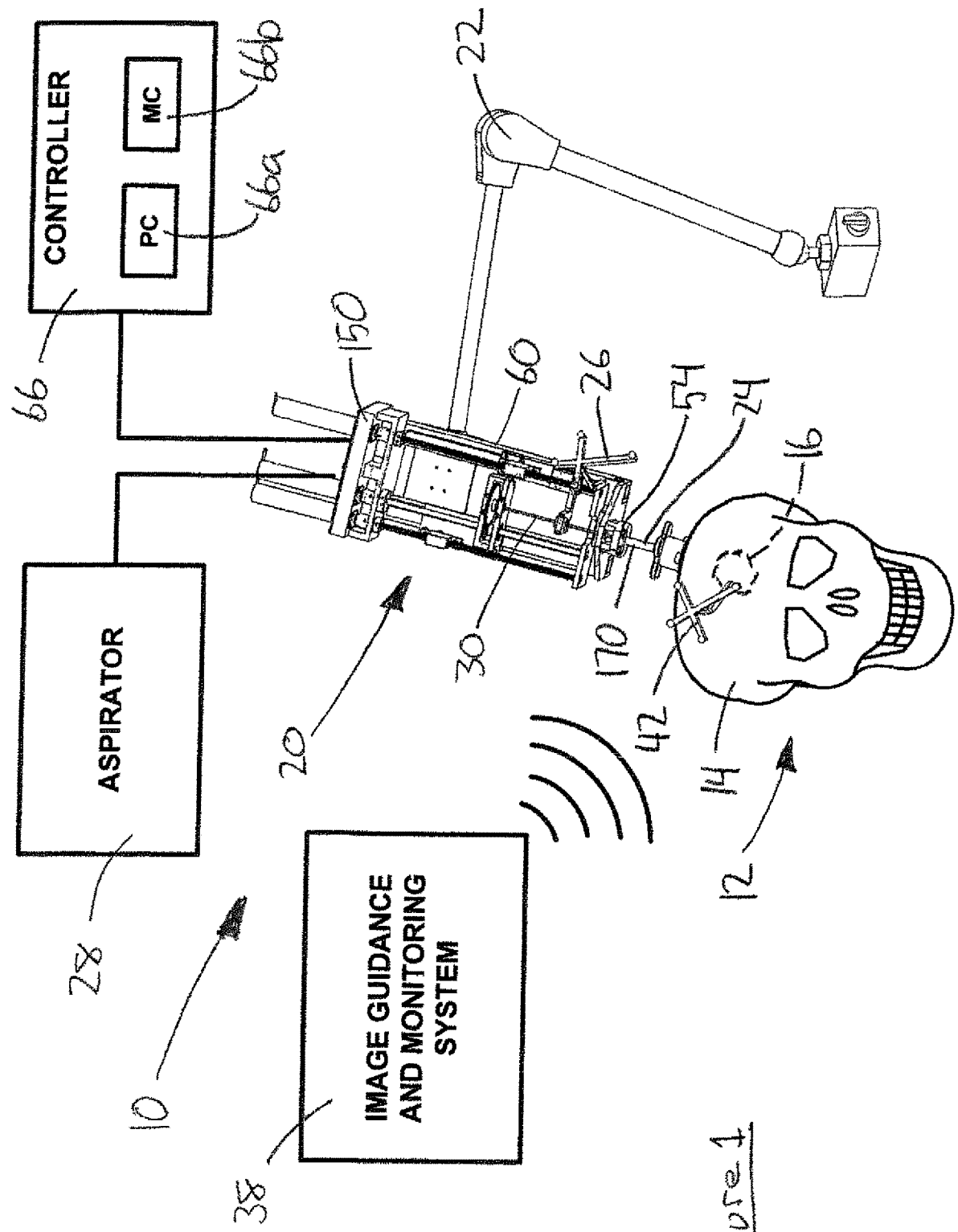
FIG. 1 is a schematic illustration of an active cannula robot system, according to an aspect of the invention.
Figure 2:
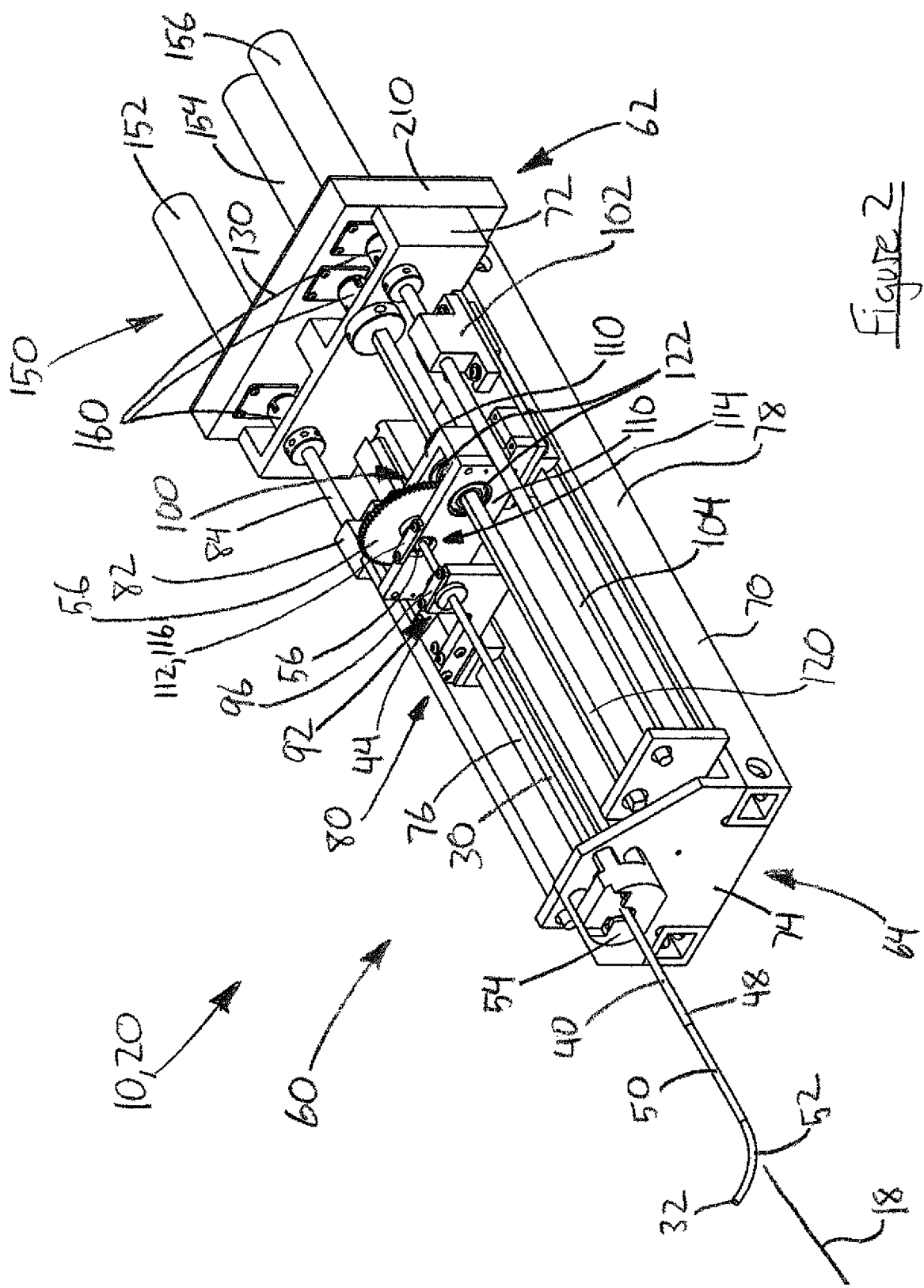
FIGS. 2 and 3 are perspective views of an active cannula robot that forms a portion of the system of FIG. 1.
Figure 3:
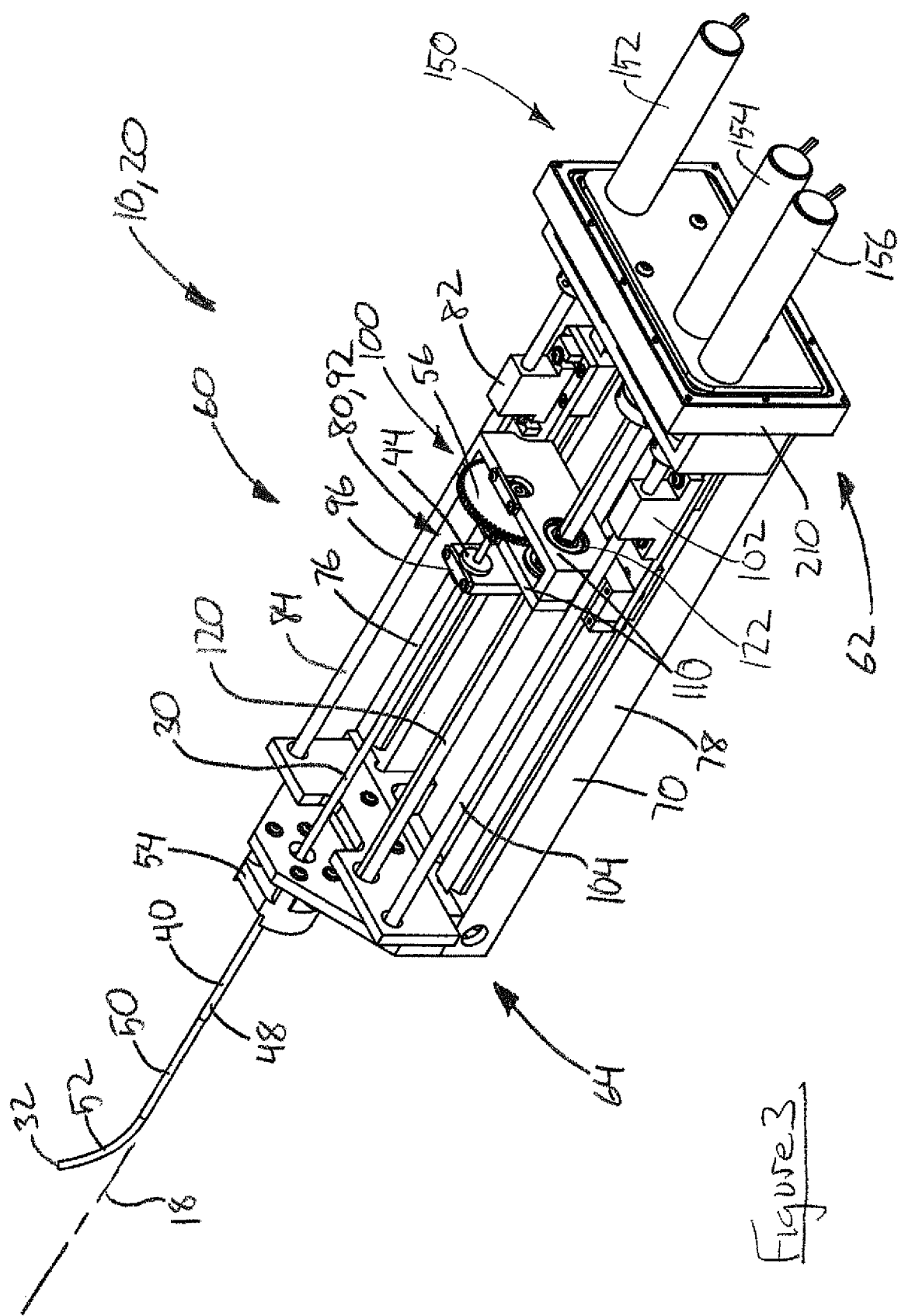
Figure 4:
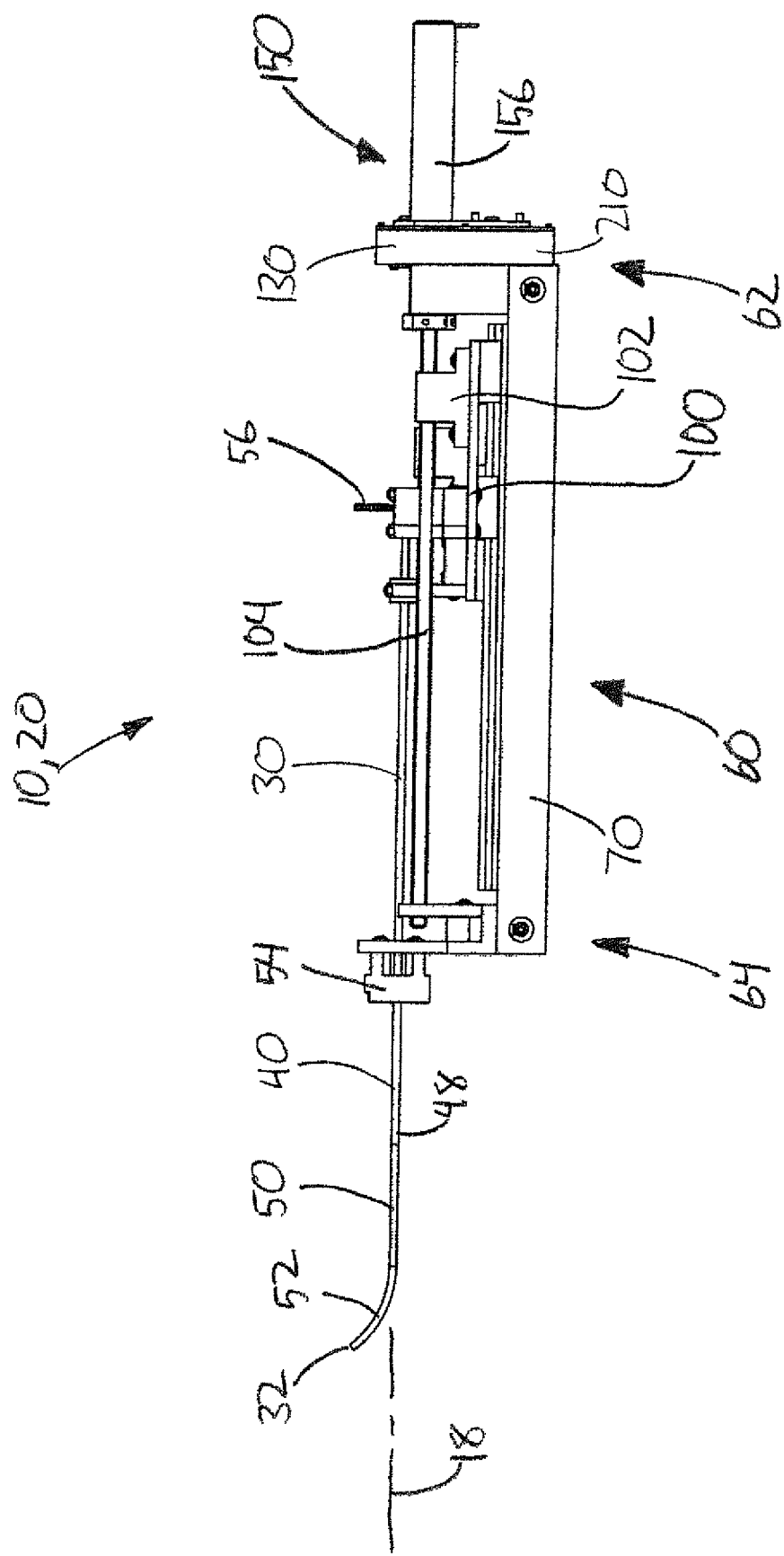
FIG. 4 is a side elevation view of the active cannula robot.
Figure 5:
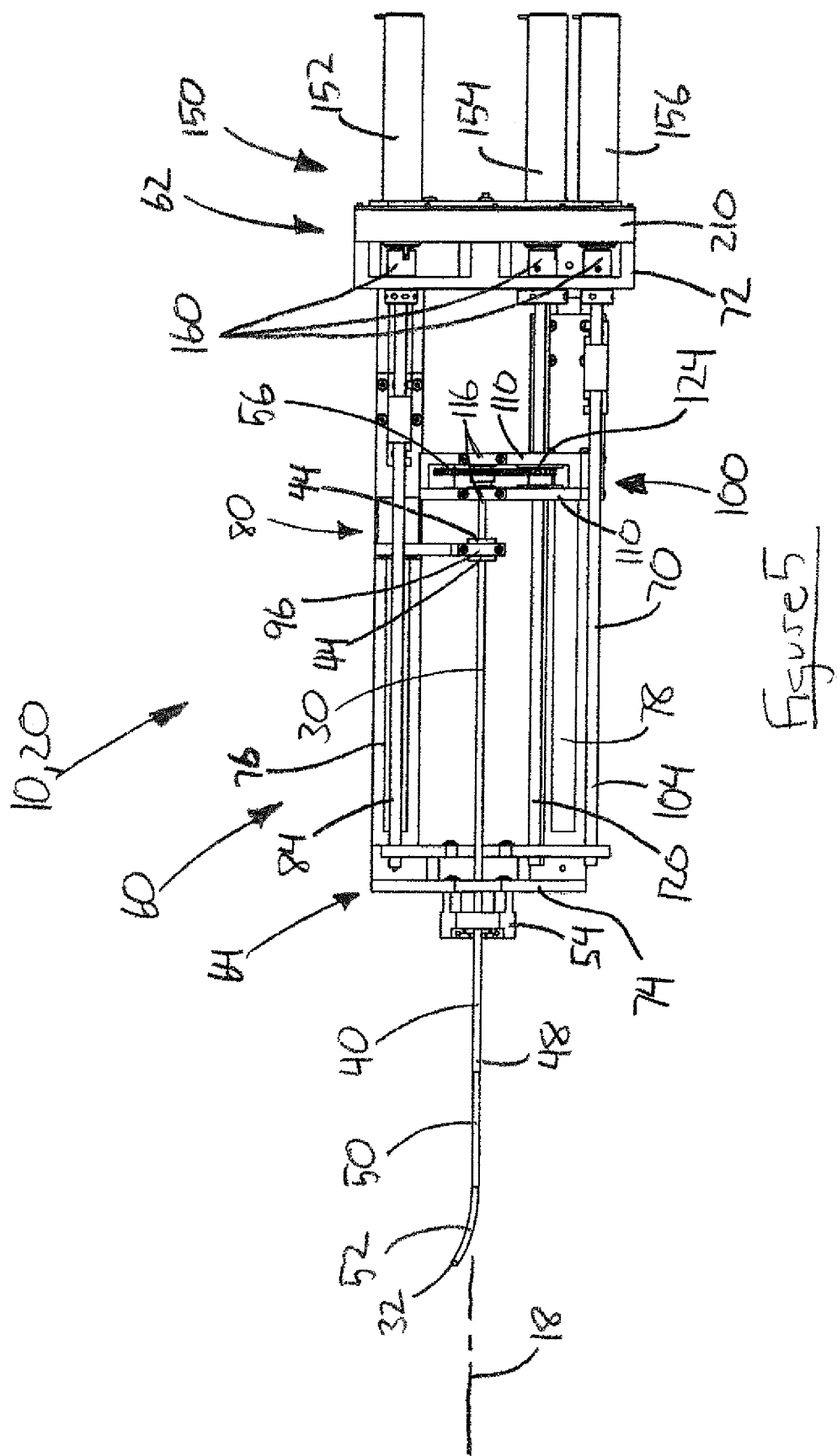
FIG. 5 is a top plan view of the active cannula robot.
Figure 6:
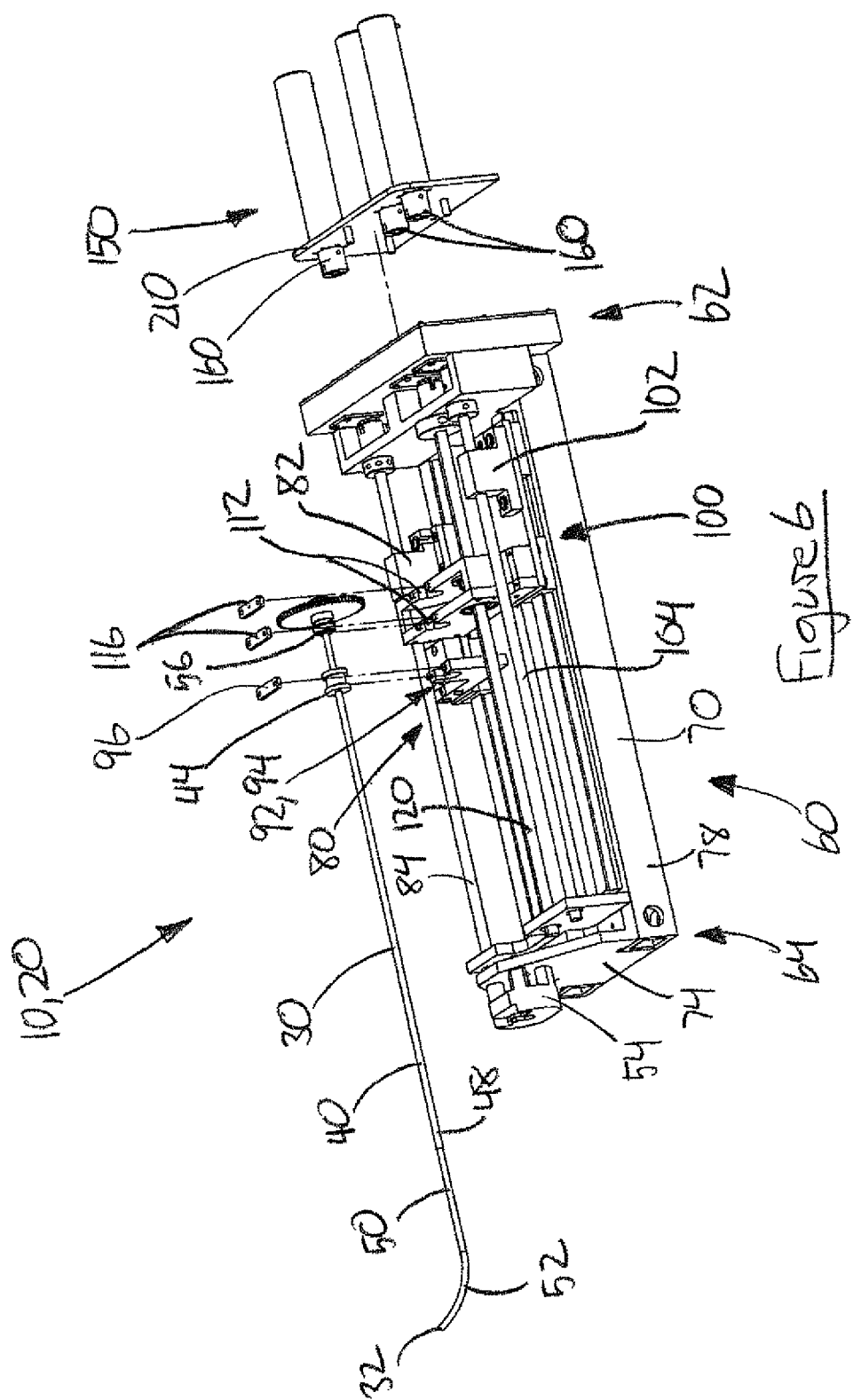
FIGS. 6 and 7 are partially exploded perspective views of the active cannula robot.
Figure 7:
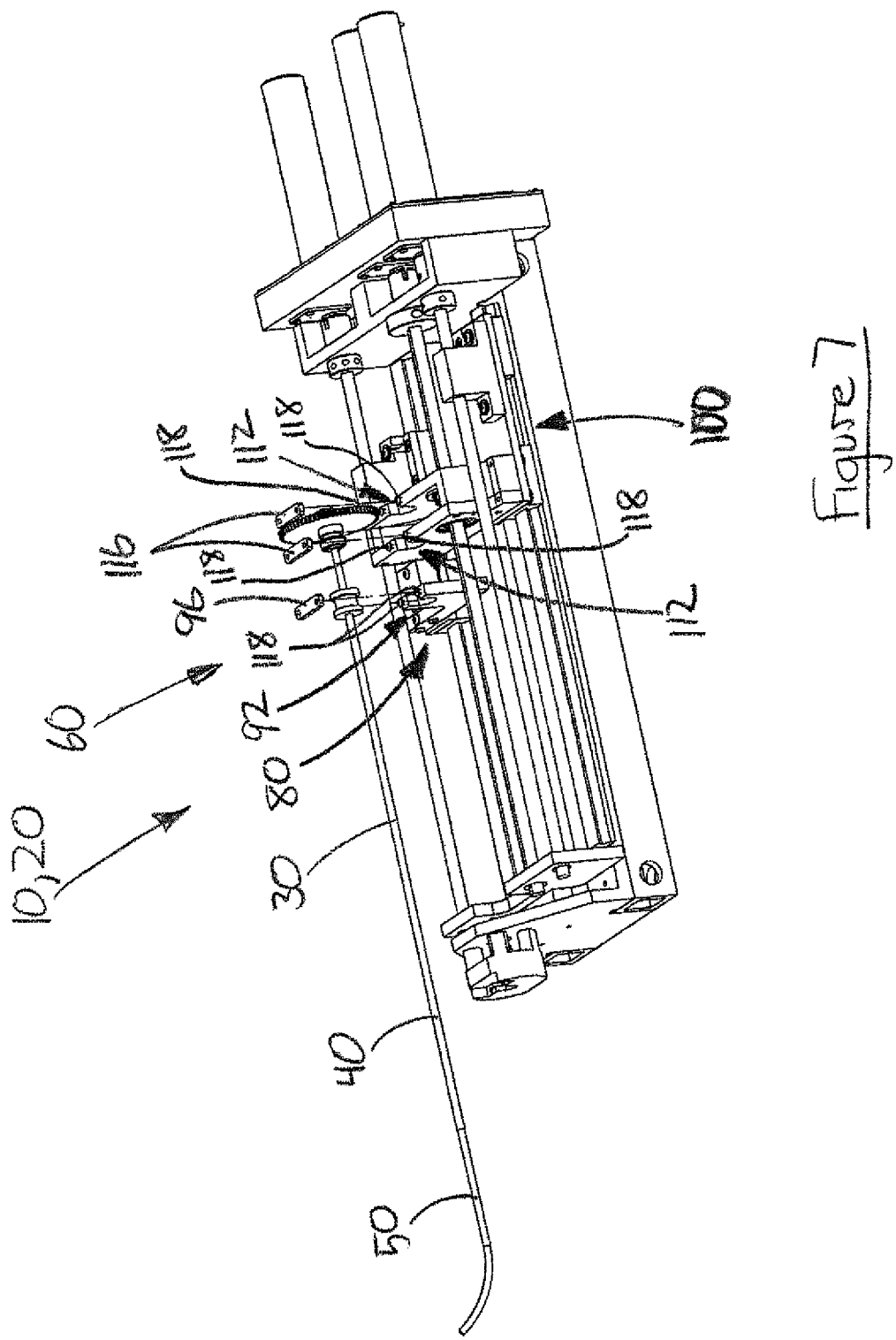

FIG. 1 illustrates an example of a robotic system 10 that can be used to treat a target at a worksite in a patient 12. In an example implementation, the system 10 can be used in a neurosurgical implementation in which the target is a clot 116 resulting from an ICH. The system 10 includes a concentric tube robot 20 mounted on a passive articulated support arm 22. For the example neurosurgical implementation described herein, a trajectory guide 24 is attached to the patient's skull 14 and is used to guide the robot 20 along a desired trajectory. A reference frame 26 is rigidly attached to the robot 20 and is used to track movement of the robot relative to the patient 12 via an image guidance and monitoring system 38. The support arm 22, trajectory guide 24 and reference frame 26 help maintain the robot 20 at a specific predetermined position and orientation relative to the target, e.g. the ICH clot 16, in the patient 12. The position and orientation are determined through image mapping of the patient 12, and the position, orientation, and shape of the target in the patient, to place the robot 20 in a position relative to the patient suited to treat the clot with the robot 20.

The system 10 includes a controller 66 that performs two basic functions: 1) performing cannula tube design/selection algorithms, and 2) controlling the operation of the robot 20 to perform a surgical operation. For simplicity, the controller 66 described herein performs both of these functions. In one implementation, the controller 66 includes a computer 66a and a motor controller 66b (see FIG. 1). The computer 66a alone can perform the tube selection algorithms described herein, and can interface with the motor controller 66b to control operation of the robot as described herein. These functions could be separated, however, and the system 10 could, for example, include one computer for performing the tube design/selection algorithms and another different computer for controlling operation of the robot 20.

The computer 66a can be any suitable computerized device having processing and memory capabilities sufficient to perform the functions described herein. For instance, the computer 66a can be a desktop computer, notebook computer, or an application specific machine that combines the computer and motor control functionality of the system 10. The components of the controller 66, i.e., the computer 66a and the motor controller 66b, can be adapted for wired or wireless communication.

In an example implementation, the computer 66a is a personal computer (e.g., an Intel® Pentium-based PC) and a standard motor controller that the computer interfaces. The motor controller 66b can be a standard motor controller or amplifier, such as a Galil® DMC Series motor controller/amplifier, which is manufactured by and commercially available from Galil Motion Control, Inc. of Rocklin, Calif. In this implementation, the computer 66a can be connected motor controller 66b via a wired Ethernet connection.

In this arrangement, the high-level motor control calculations are performed by the computer 66a using custom software applications generated using commercially available software, such as Matlab® (Mathworks, Inc. of Natick, Mass.) and/or a compilable programming language such as C or C++. These high-level algorithms generate robot control instructions in the form set points, indicating desired motor positions, that are sent to the controller 66b. The controller 66b can perform low-level control functions (e.g., closed loop PID control) and generate amplified signals to drive the motors to the set points received from the computer 66a.

Those skilled in the art will appreciate that the design/selection calculations and robot control algorithms described herein can be implemented in a wide variety of manners incorporating the use of various computer and motor control equipment. These description of the controller 66, the computer 66a, and the motor controller 66b are meant in no way to limit those options.

Referring generally to FIGS. 2-7, according to one aspect of the invention, the robot 20 includes two concentric tubes—an outer tube 40 and an inner tube 50 which, together, can be referred to herein as an active cannula 30. The outer tube 40 is a straight, stiff tube made of stainless steel. The outer tube 40 can act as a needle and therefore can be referred to as a "needle tube" or "straight needle" component of the active cannula 30. The inner tube 50 has a precurved distal end portion 52 and is made of a superelastic material, such as a nickel-titanium alloy ("nitinol"). The inner tube 50 can be operatively connected to an aspirator 28 and therefore can serve as and be referred to as an "aspiration tube" of the active cannula 30.

The inner tube 50 is retractable into the outer tube 40. As the curved end 52 of the inner tube 50 enters and passes through the outer tube 40, it straightens as it conforms to the shape of the outer tube. Due to the superelastic characteristics of its nitinol construction, the curved end 52 returns to its curved configuration as it exits the from the distal end of the outer tube 50. The active cannula 30 has a tip 32 defined by the terminal distal end or tip of the inner tube 50. In its use for ICH evacuation, the tip 32 can be referred to as an aspiration tip.

The robot 20 can be capable of controlling three degrees of freedom ("3 DOF") of the active cannula 30 through individual control of the concentric tubes 40 and 50. For instance, the robot 20 can control insertion, retraction, and rotation of the inner tube 50. Since the outer tube 40 is a straight needle, the ability to control its rotation is not important, so the robot 20 may be configured to control only its translational movement (i.e., its insertion and retraction) along the longitudinal axis 18 of the robot 20 and active cannula 30. In the example implementation, the outer tube 40 is configured to act as a needle and proceed along a straight path to deliver its tip to the location of the ICH. Once the outer tube 40 is positioned at the ICH location, the inner tube can be systematically inserted, retracted, and rotated robotically to move the tip 32 through the clot so that the clot can be debulked via suction applied by the aspirator 28.

The robot 20 includes an actuation unit 60 in which the active cannula 30 is mounted and an actuation unit in the form of a motor assembly or pack 150 that is connectable with the actuation unit at a rear or "motor" end 62 thereof. The motor pack 150 is operable to apply the motive force for individually actuating the concentric tubes 40, 50 to control movement of the active cannula 30, which extends outward from an opposite front or "robot" end 64 of the actuation unit 60.

The actuation unit 60 includes a frame 70 that has a generally box-shaped configuration. A rear plate 72 defines the rear end of the frame 70 and the motor end 62 of the actuation unit 60. A front plate 74 defines the front end of the frame 70 and the robot end 64 of the actuation unit 60. First and second rails 76, 78 extend between and interconnect the front and rear plates 72, 74 to thereby form the frame 70. The longitudinal axis 18 of the robot 20 extends longitudinally through the actuation unit 60, parallel to the rails 76, 78 and coaxially through the concentric tubes 40, 50 of the active cannula 30.

The outer tube 40 includes a hollow tubular structure that forms an inner lumen of the straight needle in through which the inner tube 50 extends. A hub 44 is secured to a proximal end portion of the outer tube 40 opposite the distal surgical end 48 of the tube. The inner tube 50 includes a hollow tubular structure that forms the cannula tube. A gear 58 is sandwiched between two hubs 56, all of which are secured to a proximal end portion of the inner tube 50 opposite the distal, surgical curved end portion 52 of the tube.

The actuation unit 60 includes an outer tube carrier 80 that is attached or otherwise connected to the first rail 76 for sliding movement along the first rail in opposite directions parallel to the axis 18. The movement of the outer tube carrier 80 along the first rail 76 can be facilitated by a suitable bushing or bearing structure. The outer tube carrier 80 includes a driver block 82 through which a first shaft 84 extends. The first shaft 84 has opposite end portions that are mounted or otherwise secured to the end plates 72, 74 by means, such as bushings or bearings, that permit the shaft to rotate. A portion of the first shaft 84 has outer (male) threads that cooperate with inner (female) threads on the driver block 82 so that rotation of the shaft imparts linear movement of the driver block, and thus the outer tube carrier 80, along the first rail 76. The direction that the outer tube carrier 80 travels is dictated by the direction in which the first shaft 84 rotates.

The outer tube carrier 80 includes a transversely extending support plate 90 that includes a tube mount 92 for receiving and supporting the outer tube 40. In the example embodiment of FIGS. 2-7, the tube mount 92 includes a recess 94 for receiving the hub 44 of the outer tube 40 and a retainer plate 96 for securing the hub in the recess. The retainer plate 96 can be secured by known means, such as threaded fasteners. When secured in the tube mount 92, the outer tube 40 is positioned extending along the axis 18. The outer tube 40, secured to the outer tube carrier 80 is thus moveable with the carrier along the axis 18 in response to rotational movement of the first shaft 84.

The actuation unit 60 also includes an inner tube carrier 100 that is attached or otherwise connected to the second rail 78 for sliding movement along the second rail in opposite directions parallel to the axis 18. The movement of the inner tube carrier 100 along the second rail 78 can be facilitated by a suitable bushing or bearing structure. The inner tube carrier 100 includes a driver block 102 through which a second shaft 104 extends. The second shaft 104 has opposite end portions that are mounted or otherwise secured to the end plates 72, 74 by means, such as bushings or bearings, that permit the shaft to rotate. A portion of the second shaft 104 has outer (male) threads that cooperate with inner (female) threads on the driver block 102 so that rotation of the shaft imparts linear movement of the driver block, and thus the inner tube carrier 100, along the second rail 78. The direction that the inner tube carrier 100 travels is dictated by the direction in which the second shaft 104 rotates.

The inner tube carrier 100 includes a pair of spaced, parallel, transversely extending support plates 110, each of which include a tube mount 112 for receiving and supporting the inner tube 50. The tube mounts 112 are axially aligned with each other. Each mount 112 includes a recess 114 for receiving one of the hubs 56 of the inner tube 50. One or both of the mounts 112 includes a retainer 116, such as a plate, for securing its associated hub 56 in the recess. One such retainer plate 116 can be sufficient to secure the inner tube 50 to the inner tube carrier 100. The retainer plate 116 can be secured by known means 118, such as threaded fasteners, e.g., screws. When the inner tube 50 is secured in the tube mounts 112, the gear 58 is positioned between the support plates 110.

When the inner tube 50 is secured in the tube mounts 112, it is also positioned extending along the axis 18 and can thereby be positioned coaxially within the inner lumen of the outer tube 40. The inner tube 50, secured to the inner tube carrier 100, is thus moveable with the carrier along the axis 18 in response to rotational movement of the second shaft 104. The inner tube 50 is also rotatable relative to the inner tube carrier 100 when secured in the tube mounts 112. The inner tube 50 can thus be rotated via the gear 58. The outer tube carrier 80 and inner tube carrier 100 together carry the active cannula 30.

A third shaft 120 has opposite end portions that are mounted or otherwise secured to the end plates 72, 74 by means, such as bushings or bearings, that permit the shaft to rotate. The third shaft 120 extends through the support plates 110, adjacent the inner tube 50. The support plates 110 include guides 122, such as bearings, through which the third shaft 120 extends. The guides 122 receive stabilize the third shaft 120 radially, while permitting rotation of the shaft relative to the support plates 110 and also permitting the support plates to move linearly relative to the shaft along its length. To accomplish this, the third shaft 120 can, for example, have a non-circular (e.g., square) cross-section, and the guides 122 can have a bearing structure in which their inner rings have a corresponding non-circular opening through which the third shaft extends. In this configuration, the guides 122 can slide freely over the third shaft 120 when the support plates 110 move longitudinally, while their bearing structures simultaneously support the shaft for rotation.

The third shaft 120 includes a gear 124 that is positioned between the support plates 110 and that engages the gear 58 of the inner tube 50. Rotation of the third shaft 120 thus imparts rotation to the inner tube 50. The gear 124 is fixed to the third shaft 120 in a manner such that it rotates with the shaft while at the same time is free to slide axially along the length of the shaft. The gear 124 can, for example, have a non-circular (e.g., square) opening that corresponds with the aforementioned non-circular cross-section of the third shaft 120 without being fixed to the shaft. Due to this configuration, the gear 124 can slide freely along the length of the third shaft 120, which allows it to maintain its engagement with the gear 58 as the inner tube carrier 100 moves along the length of the actuation unit 60. By maintaining this engagement, the gear 124 can impart rotation to the gear 58 to rotate the inner tube 50 at any axial position of the inner tube carrier 100. In fact, this configuration can allow the third shaft 120 to maintain its ability to impart rotation to the inner tube 50 even while the inner tube carrier 100 and the inner tube 50 itself is moving axially.

The motor pack 150 includes a first motor 152 for actuating the first shaft 84, a second motor 154 for actuating the second shaft 104, and a third motor 156 for actuating the third shaft 120. The motors can be of any desired configuration, such as a brushless DC stepper motor configuration. The motors 152, 154, 156 are mounted on one side of a motor plate 210, and each include a respective motor coupling 160 that extends through and protrudes from an opposite side of the plate. A mechanism 164 such as latch, lock, or fastener(s), secure the motor pack 150 to the actuation unit 60 by interconnecting the motor plate 210 to the rear plate 72. Connecting the motor pack 150 to the actuation unit 60 engages the motor couplings 160 with their respective shafts to thereby couple the motors 152, 154, 156 to the shafts 84, 104, 120. In one example, the motor couplings 160 can be respective portions of Oldham couplings, which are well known in the art as being shaft couplings that are simple, secure, and reliable.

The motor pack 150 is operable to actuate the active cannula 30. The first motor 152 is operable to control insertion and retraction of the outer tube 40. The second motor 154 is operable to control insertion and retraction of the inner tube 50. The third motor 156 is operable to control rotation of the inner tube 50.

The actuation unit 60 is designed to be both sterilizable and biocompatible. The actuation unit 60 is constructed entirely from autoclavable and biocompatible components. All of the materials used to construct the actuation unit 60 are either biocompatible polymers (e.g., Ultem® or PEEK®), stainless steel (which would be passivated before clinical use), aluminum (which would be anodized before clinical use), or nitinol (in the case of the inner tube 50). The hubs 46, 56 and the gear 58 are secured to their respective tubes 40, 50 using a biocompatible and autoclavable bonding agent or glue (e.g., Loctite®, M-21 HP medical device epoxy agent). All of these materials can withstand sterilization in an autoclave.

Referring to FIGS. 8-10, the motor pack 150 also includes a bag ring 130 for securing a sterile bag 132 to the motor plate 210. With the sterile bag 130 connected as shown in FIG. 8, the shafts 84, 104, 120 are left exposed for connection with the motor couplings 160. As shown in FIG. 10, cover plates 166 can be slid over the motor couplings 160 and secured to the motor plate 210 so as to create a tortuous path P (see FIG. 10) between the non-sterile motor pack 150 in the sterile bag 132 and the sterile actuation unit 60.

The sterile bag 132 in combination with the tortuous path P created by the cover plates 166 can provide a sterility barrier that is sufficient to permit use of the robot 20 in a surgical environment such as an operating room. To set up the robot 20 in the operating room, The actuation unit 60, including the robot tubes 40, 50, are first autoclaved to sterilize the unit. The sterile bag 132 is attached to the motor pack 150 using the bag ring 130, the motor couplings 160 are coupled to the shafts 84, 104, 120, the motor pack 150 is attached via the motor plate 210, and the cover plates 166 are installed. The sterile bag 132 is then pulled over the motor pack 150 and sealed using means, such as sterile tape. The motor pack 150 is thereby isolated from the sterilized actuation unit 60.

Inner Tube Hot-Swap Feature

According to one aspect, the robot 20 includes a quick-release "hot-swap" feature that allows for interchangeably installing inner tubes 50 having different features, such as curvature, radius, stiffness, or a combination of these features, during a robotic surgical procedure without dismantling or de-constructing the robot 20 and without disturbing the arrangement of the system 10 and the position/orientation of the robot with respect to the patient 12. Owing to the configuration of the inner tube carrier 100, specifically the tube mounts 112, the inner tube 50 can be released for removal and replacement by removing a fasteners 118 and pivoting or removing the retainer plates 116. The inner tube 50 can first be retracted fully so that the tube can flex as it is removed from the outer tube 40.

To insert another inner tube 50, its curved end 52 is inserted into the inner lumen 44 of the outer tube 40 from the proximal end adjacent the gear 56 and advanced until the hubs 56 come into alignment with the mounts 112 in the support plates 110. The hubs 56 are placed in the mounts 112, the retainer plates 116 are placed back into position, and the fasteners 118 are reinstalled to secure the inner tube 40 in the mounts. In a configuration where the fasteners 118 are thumb screws, the removal of the retainer plates 116 is provides convenient and expedient. Alternative means, such as a manually actuated latching mechanism, could also be used.

Emergency Release Feature

Figure 11:
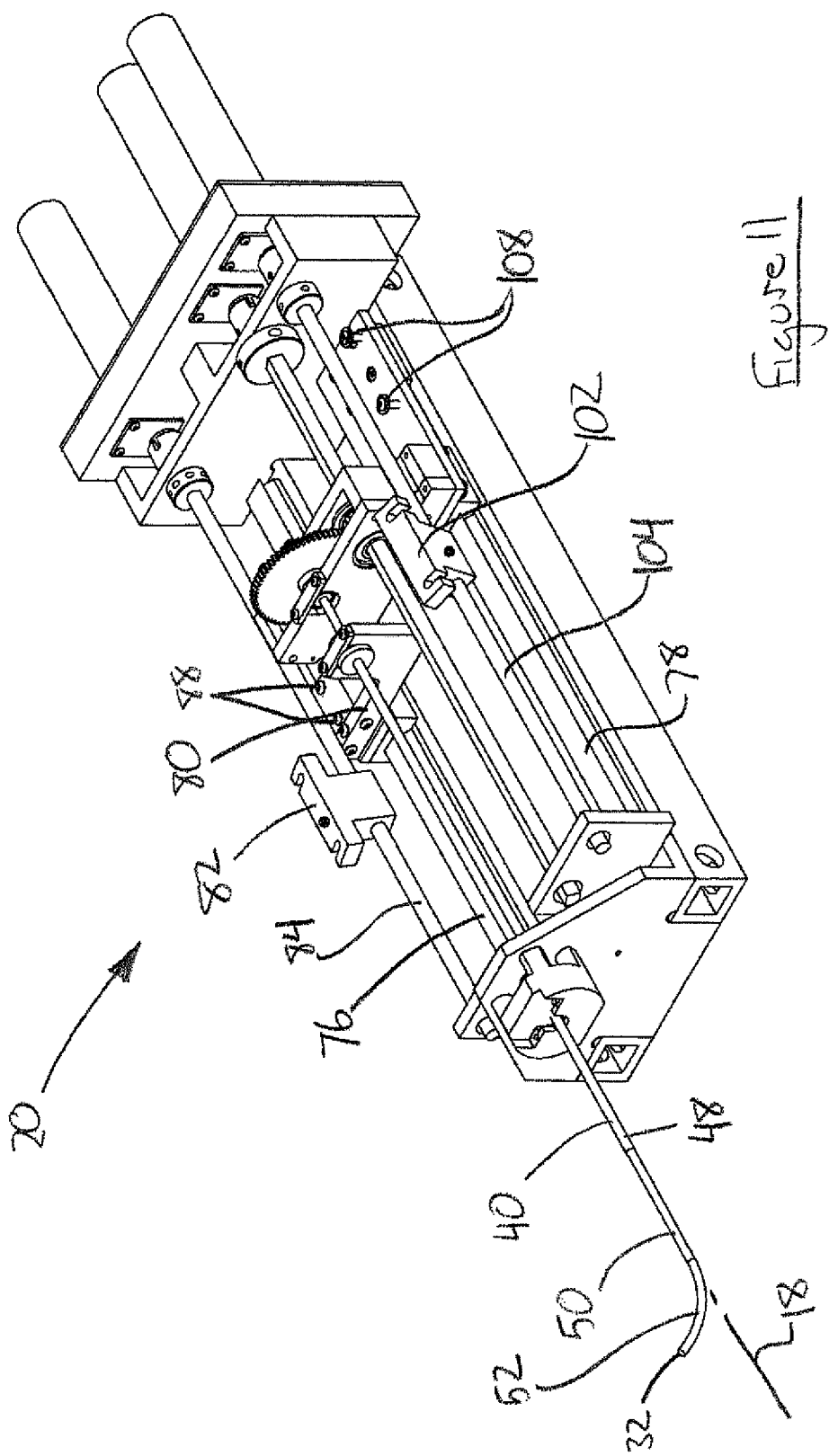
FIG. 11 is a perspective view illustrating an emergency release feature of the active cannula robot.
Figure 12:
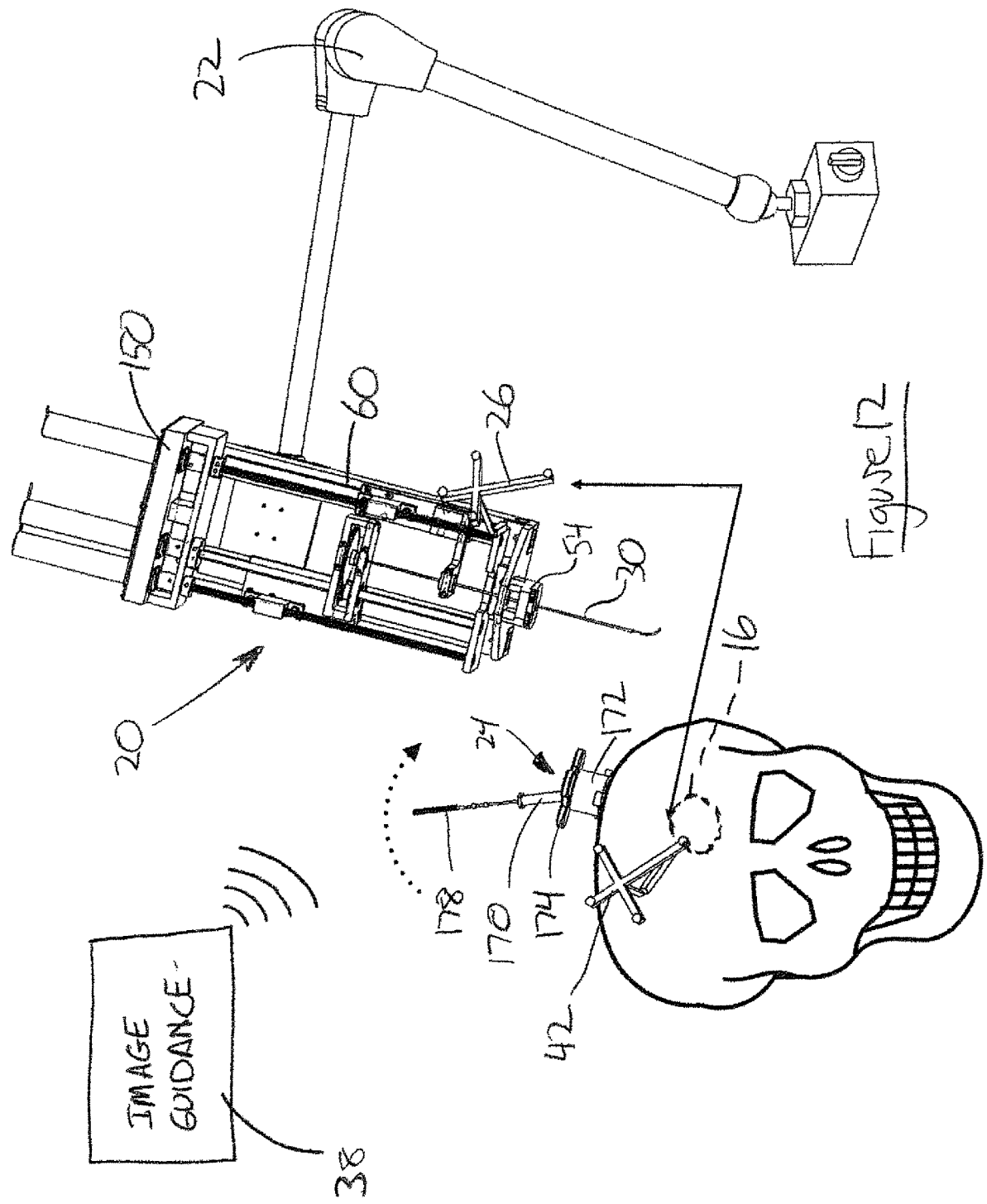
FIG. 12 is a schematic illustration of the system of FIG. 1 illustrating an alignment feature of the system.
Figure 15A:
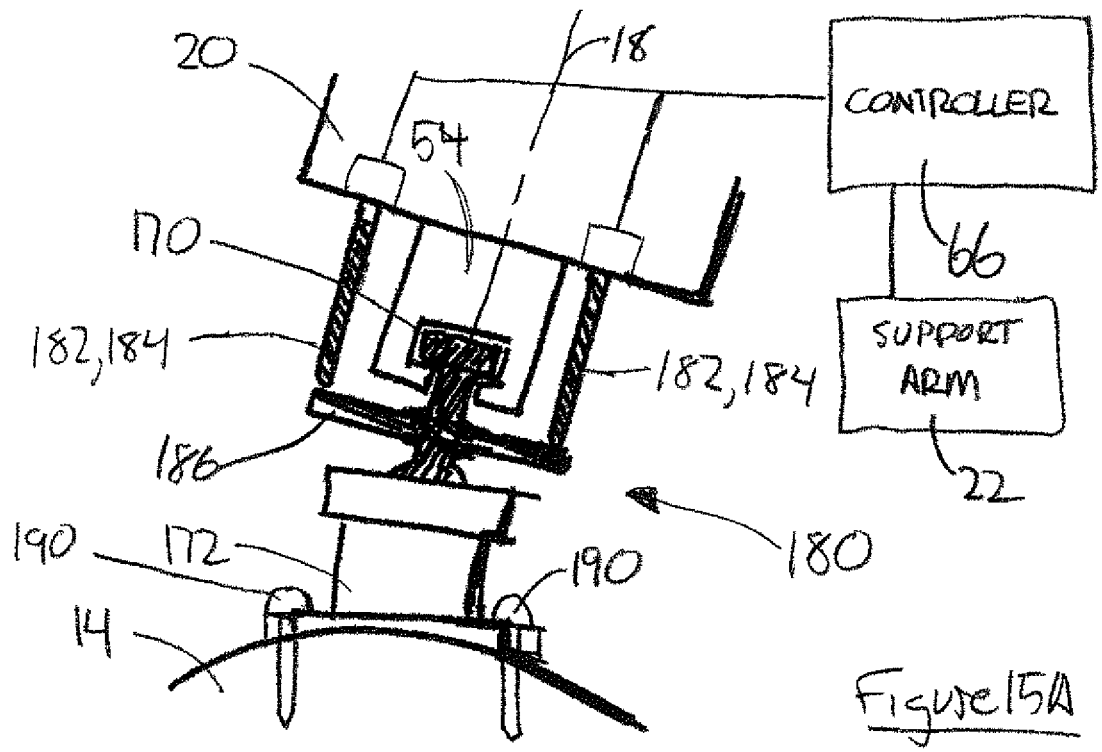
Figure 15B:
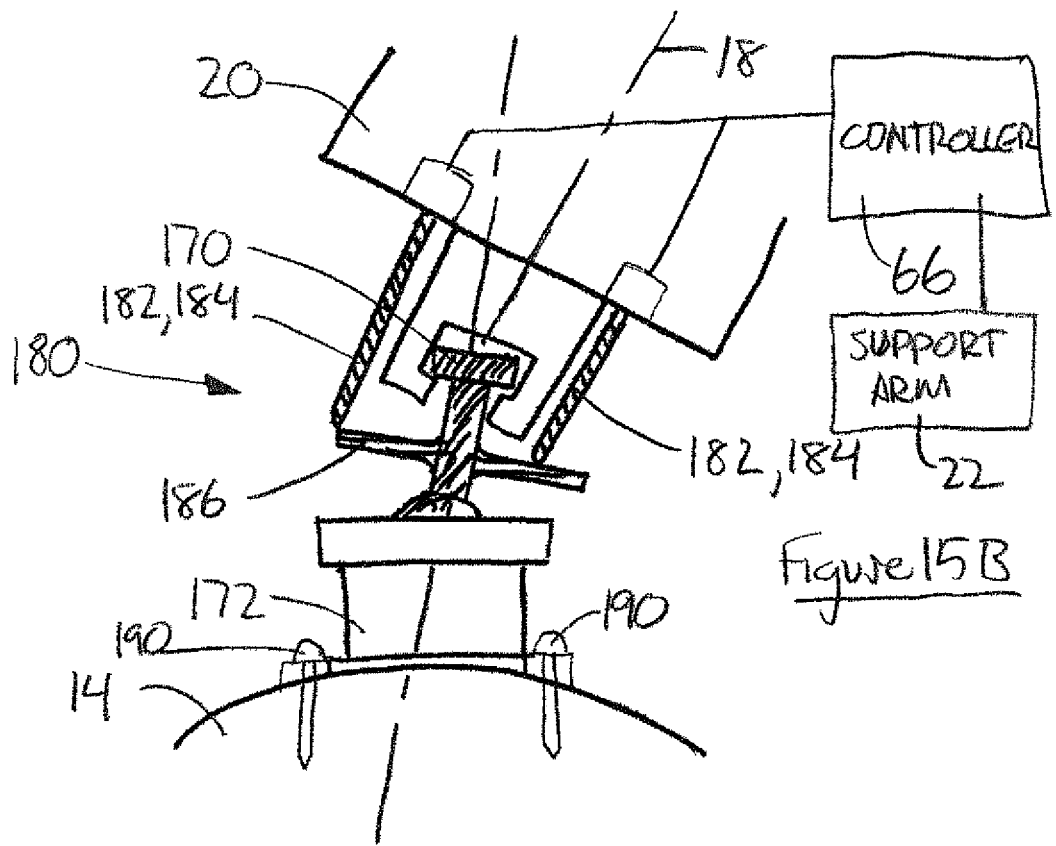

Referring to FIG. 11, according to another aspect, the robot 20 includes an emergency release feature that allows for the quick removal of both the inner tube 50 and the outer tube 40. The driver block 82 is secured to the outer tube carrier 80 by releasable fastening means 88, such as a thumb screw. The driver block 102 is secured to the inner tube carrier 100 by releasable fastening means 108, such as a thumb screw. The thumb screws 88, 108 provide a convenient and expedient means by which to disengage the driver blocks 82, 102 from the carriers 80, 100. The thumb screws 88, 108 could have alternative configurations, such as alternative threaded fasteners or a manually actuated latching mechanism. In an emergency situation where the robot 20 needs to be retracted from the patient 12 quickly, the thumb screws 88, 108 are operated to disengage the driver blocks 82, 102 from the carriers 80, 100. This decouples the tube carriers 80, 100 from the shafts 84, 104, which allows the carriers to slide freely along the rails 76, 78. The tubes 40, 50 can then be retracted manually from the patient 12 in a quick and efficient manner simply by manually sliding the carriers 80, 100 along the rails 76, 78.

Image Guided Positioning

The system 10 can incorporate an image guidance system 38 to position the robot 20 relative to the patient 12. This positioning is described herein as it relates to the example implementation in which the system 10 is used to evacuate an ICH clot. Those skilled in the art will appreciate that similar procedures can be performed where the system 10 is used to perform other procedures.

Prior to the ICH clot removal procedure, computed tomography (CT) medical images of the patient and the ICH are acquired. Registration is accomplished using a surface scan of the patient's face, which is then matched to the corresponding surface in the CT image volume. A reference frame 42 mounted to the patient's skull allows the image guidance system 38 to monitor the position and alignment of the patient 12, specifically the patient's head and the clot 16. Since the active cannula 30 is introduced onto the patient's brain with the inner tube 50 retracted, the delivery of the straight needle tube 40 is essentially identical to delivery of a biopsy needle. This being the case, known conventional image guided neurosurgical systems presently used to align and introduce straight biopsy needles can also be used to align and introduce the active cannula robot 20. One example of a known image guidance system 38 that can be used to align and monitor the active canula robot 20 is a StealthStation® system using Navigus® biopsy hardware, which is available commercially from Medtronic, Inc., USA. Other commercially available image guidance systems can be used. The reference frame 26, which is attached to the robot 20, can be adapted to work with the chosen image guided neurosurgical system in order to facilitate monitoring the position and alignment of the robot.

Referring to FIG. 1, the trajectory guide 24 includes a trajectory stem 170 that is mounted on the patient's skull and through which the active cannula 30 extends. The trajectory stem 170 is selected to work in conjunction with the image guidance system 38 and therefore can be in the form of custom or proprietary hardware specifically designed for use with the image guidance system. The trajectory stem 170 can, for example, be one that is included in the aforementioned Navigus® line of neurosurgical biopsy hardware. The trajectory stem 170 defines the path or trajectory along which the active cannula 30 extends from the robot 20 through the skull and into the brain.

In use, the robot 20 is positioned relative to the patient 12 so that the active cannula 30 extends along the axis 18 through the trajectory stem 170 (see FIG. 1). The trajectory stem 170 is configured to connect with a base 172 that is connectable with the patient's skull, e.g., via screws. A locking ring 174 facilitates the connection between the trajectory stem 170 and the skull-mounted base 172 so that the trajectory stem can direct the active cannula 30, with the inner tube 50 retracted into the outer tube 40 through the base and into the patient's skull along the desired trajectory.

To set up and align the system 10, the surgeon first creates a hole in the skull, opens the dura to expose the brain, and attaches the base 172 to the skull, e.g., using screws. The trajectory stem 170 is then snapped into the base 172 and loosely secured with the locking ring 174. An alignment probe 178, which enables visualization of the insertion trajectory via the chosen image-guidance system, is inserted into the trajectory stem 170. Image guidance is used to align the trajectory stem 170 by pivoting the stem in the base 172 until the trajectory of the stem is aligned with the desired ICH clot target 16. The locking ring 174 is then tightened to fix the position of the trajectory stem 170, after which the alignment probe can be removed.

Next, the robot 20, attached to the support arm 22, is moved into the surgical field, and the front plate 74 of the actuation unit 60 is coupled to the trajectory stem 170 by means, such as a bracket/clamping mechanism 54. The robot 20 can then be operated to move the active cannula 30 through the trajectory stem 170 along the desired trajectory into the brain. The robot 20 can be operated, for instance, to first insert the outer tube 40 into the brain to position its tip at the ICH location or in the ICH itself. Then, the robot 20 can be operates to insert and/or rotate the inner tube 50 in the ICH to remove the clot. During operation of the robot 20, the insertion, retraction, and rotation of the tubes 40, 50 can be monitored using CT medical imaging via the reference frame 26.

Active Trajectory Maintaining Configuration

The trajectory stem 170 can have an alternative configuration that facilitates maintaining the alignment of the robot 20 with the skull-mounted base 172. The weight and size of the robot 20 is large enough that a misalignment between the trajectory stem 170 and the base 172 could result in the application of excessive forces to the bone screws 190 which mount the base to the skull. Referring to FIGS. 15A-15D, the trajectory stem 170 and the base 172 can include an active alignment system 180 that ensures proper alignment between the stem and base without applying undue stress to the bone screws 190.

This active alignment system 180 could replace the locking ring with a predetermined number of sensors 182 spaced radially about the axis 18 and connected to the trajectory stem 170. For example, the alignment system 180 could include three sensors 182, spaced at 120° intervals about the robot axis 18. The sensors 182 are configured to deflect in response to a misalignment between the robot 20 and the trajectory stem 170. In the embodiment illustrated in FIGS. 15A-15C, the sensors 182 comprise plunger elements 184 that engage a flange 186 that extends radially outward from and perpendicular to the trajectory stem 170. Each sensor 182 is configured to produce a signal representative of the deflection of the sensor, in this case the plungers 184. The plungers 184 could, for example, include a strain gauge having a resistance changes in response to strain and therefore can be used to produce a signal representative of the amount of deflection undergone by the sensor 182. Alternatively, the plungers 184 could actuate a variable resistance element, e.g., a rheostat, having a resistance changes in response to strain and therefore can be used to produce a signal representative of the amount of deflection undergone by the sensor 182.

When the robot 20 and the trajectory tube 170 are correctly aligned (see FIG. 15A), the plungers 184 engage the flange 186 and deflect to an equal extent, producing similar or identical deflection signals. The differential between the sensor signals is indicative of any misalignment (see FIG. 15B). If three sensors 182 are used, these signal differentials can be used to calculate/triangulate the direction and magnitude of the misalignment. This misalignment magnitude and direction can be displayed visually, e.g., via the controller 66 (computer 66a) in real time, so that adjustments can be made with visual feedback.

Once a misalignment is identified measures should be made to relieve the stresses on the interface of the base 172 with the skull due to the misalignment. One possible solution would be a robotic base (replacing the support arm 22) which could actively move or position the robot 20 to prevent or remedy a misalignment. Instead of mounting the robot 20 on a rigid, fixed, passive support arm 22, the robot could itself be mounted on an active positioning mechanism 184 that can adjust the position of the robot to maintain the trajectory of the active cannula 30, e.g., via servo motors. The sensors 182 could be used as inputs to a controller that is configured to control the operation of the positioning mechanism 184. In use, the robot 20 could be initially aligned via manual control of the positioning mechanism 184. The inputs from the sensors 182 could then be used as a setpoint that the controller could maintain via closed loop control of the positioning mechanism 184. In this manner, the proper trajectory can be maintained without compromising the connection of the base 174 to the skull 14.

An alternative solution is shown in FIG. 15C. In this alternative, the robot 20 includes a would be a set of padded arms 192 extending from the robot to the skull 14. These padded arms 192 would stabilize the robot 20 with respect to the skull 14. The padded arms 192 could be anchored to the skull 14 via a series of straps 194 that extend around the skull. In this manner, misalignment forces between the robot and skull would be distributed over a large area of the skull 14 by the padded arms 192 instead of the small area of the bone screws 190 that attach the base 172 to the skull. The axial position of the padded arms 192 can be adjustable to control the misalignment detected via the sensors 182. These adjustments could be active, i.e., computer controlled via the controller 66 operatively connected to appropriate servo motors 196 to minimize the stress/maintain proper robot alignment in response to the sensor 182 signals, or adjustable manually, e.g., via knobs.

Alternative Torque Transmission Configuration

In certain scenarios, it may be necessary to position the actuation mechanism 60 a significant distance from the work space. The inner tube 50 can be considered to include two basic sections: a working end that performs the ICH evacuation and a transmission section that translates and rotates the working end. The working end of the inner tube 50 is the curved end portion 52, which is purposely constructed of an inherently flexible material due to manner in which it is utilized in the operation of the active cannula 30. The transmission section is simply the portion of the inner tube 50 that extends from the curved portion 52 to the actuator assembly 60. As described previously, the transmission section can be constructed of the same material that is used to construct the working end and therefore has the same inherent flexibility.

During use of the active cannula 30, inner tubes 50 with larger curvatures of the working section produce higher torques on the transmission section when the tube is rotated. This can lead to torsional windup in the transmission section of the inner tube 50. Torsional windup is undesirable because it distorts the shape of the inner tube 50, which can introduce uncertainty in the operation of the active cannula 30. Torsional windup can lead to a reduced workspace for the inner tube 50 because excessive windup in the tube limits the curvatures that can be implemented. Ideally, the transmission section would be rigid in order to avoid these problems.

According to one aspect of the invention, referring to FIGS. 13A-13F, a transmission tube assembly 220 couples the active cannula 30 to the actuator assembly, i.e., the motor pack 150 via the tube carriers 80, 100. The transmission tube assembly 220 includes an outer transmission tube 222 and an inner transmission tube 224. The inner transmission tube 224 is positioned coaxially within the outer transmission tube 222. An outer tube coupler 230 is fixed to the distal end of the outer transmission tube 222 and couples the outer tube 40 to the outer transmission tube. An inner tube coupler 232 is fixed to the distal end of the inner transmission tube 224 and couples the inner tube 50 to the inner transmission tube. The transmission tube assembly 220 is configured such that the inner tube 224 can slide or telescopes axially within the outer tube 222 and can also rotate about the axis 18 relative to the outer tube.

In this configuration, the inner transmission tube 224 can be adapted to include the gear 58 and hubs 56 that facilitate connection of the inner transmission tube to the inner tube carrier 100 of the actuation unit 60. Similarly, the outer transmission tube 222 can be adapted to include the hub 44 that facilitates connection of the outer transmission tube to the outer tube carrier 80 of the actuation unit 60. These connections can be facilitated, for example, by features such as a key-receiving slot 236 or a pin receiving hole 238 machined or otherwise formed in the proximal ends of the outer and inner transmission tubes 222, 224.

The outer and inner transmission tubes 222, 224 can therefore be actuated by the actuation unit 60 in the same manner that the outer and inner tubes 40, 50 in the configuration of the robot 20 illustrated in FIGS. 2-7. The outer and inner tubes 40, 50 of the active cannula 30, being coupled to the outer and inner transmission tubes 222, 224, respectively, can thus be translated and/or rotated by the actuation mechanism 60. In this configuration, the active cannula 30, including the outer tube 40 and inner tube 50, extend from the distal end of the transmission tube assembly 220. Thus, the robot 20 shown in FIGS. 2-7, fit with the transmission tube assembly 220, can deliver and operate the active cannula 30.

Robot Design and Configuration

The curved inner tube 50 can have any desired curvature, as long as that curvature is one which can be straightened completely with a maximum material strain that remains within the elastic range of nitinol, i.e., approximately 8-10%. Within these constraints, virtually any desired curvature can be achieved through the use of known heat treatment processes. For any given curvature, a workspace exists. The workspace associated with a curvature of an inner tube is the space that can be reached with the tip of that particular curved tube. The workspace of the inner tube 50 thus corresponds to the shape of the target that the active cannula 30 can access. In the example ICH clot removal implementation of the robot 20, the workspace of an inner tube 50 thus corresponds with the shape of the ICH clot that can be evacuated with that particular tube.

According to the invention, knowing the predefined curvature of the inner tube 50, the controller 66 can compute the shape of the workspace for that particular tube using a mechanics-based model. This model can be evaluated for different tube configurations to determine the workspace for that particular tube configuration. According to one aspect of the invention, given image data related to a surgical target, the controller 66 can design one or more tube configurations by solving the kinematic model systematically through a discrete set of tube parameters to identify the parameters of the tube or set or tubes that provide a desired or optimal degree coverage of the target. According to another aspect of the invention given an active cannula 30 with a finite set of inner tubes 50 each having a different pre-curved configuration and corresponding workspace, the controller 66 can evaluate the kinematic model and compare the calculated workspace to the of the target to select the tube or tubes from the subset that provide a desired or optimal degree coverage of the target.

In the illustrated implementation, the controller 66 can use the kinematic model to determine the configuration(s) of the inner tube(s) 50 so that the workspace of the active cannula 30 can treat an ICH clot. For clots with complex geometries, there may not be a combination of inner tubes 50 that offers a combined workspace capable of complete clot removal. Because of this, two or more inner tubes 50 with different curve configurations can be selected so that their combined workspace covers the required area to as complete an extent as conditions permit. For these multi-tube scenarios, the active cannula robot 20 is ideally suited to leave the outer tube 40 positioned "in situ" at the worksite while inner tubes 50 are hot-swapped and used sequentially.

Regardless of the implementation, to model the active cannula 30 the three degrees of freedom of the straight outer tube 40 and the circularly pre-curved inner tube 50 are parameterized using the variables $\rho_1$ and $\rho_2$ to describe the linear insertion distance of the outer and inner tubes, respectively. The angle $\alpha$ describes the axial angle (i.e., the angle of rotation about the axis 18) of the inner tube 50. Thus, the joint space of the active cannula 30 is $q=(\rho_1, \rho_2, \alpha)$.

Referring to FIG. 14A, the inner tube 50 is composed of an initial straight section with length Ls followed by a planar constant curvature section with length Lc with radius r. When the inner tube 50 is inserted into the outer tube 40, there are three regions to model kinematically, with lengths $l_1, l_2, l_3$ (see FIG. 14B). The mapping from joint space to configuration space parameters describing the curve of the robot (i.e., "arc parameters,") is as follows:

$$\ell_1 = \rho_1$$

$$\ell_2 = \begin{cases} \rho_2 - \rho_1 - Lc & \text{if } \rho_2 - \rho_1 > Lc \\ 0 & \text{else} \end{cases}$$

$$\ell_3 = \begin{cases} Lc & \text{if } \rho_2 - \rho_1 > Lc \\ \rho_2 - \rho_1 & \text{else} \end{cases}$$

$$\kappa_3 = r^{-1}.$$

These parameters define a forward kinematic model for the active cannula 30, $T = T_\alpha T_{12} T_3$, where:

$$T_\alpha = \begin{bmatrix} \cos\alpha & -\sin\alpha & 0 & 0 \\ \sin\alpha & \cos\alpha & 0 & 0 \\ 0 & 0 & 1 & 0 \\ 0 & 0 & 0 & 1 \end{bmatrix};$$

$$T_{12} = \begin{bmatrix} 1 & 0 & 0 & 0 \\ 0 & 1 & 0 & 0 \\ 0 & 0 & 1 & \ell_1 + \ell_2 \\ 0 & 0 & 0 & 1 \end{bmatrix}; \text{ and}$$

$$T_3 = \begin{bmatrix} 1 & 0 & 0 & 0 \\ 0 & \cos(\kappa_3\ell_3) & -\sin(\kappa_3\ell_3) & \frac{\cos(\kappa_3\ell_3)-1}{\kappa_3} \\ 0 & \sin(\kappa_3\ell_3) & \cos(\kappa_3\ell_3) & \frac{\sin(\kappa_3\ell_3)-1}{\kappa_3} \\ 0 & 0 & 0 & 1 \end{bmatrix}$$

For the circularly curved inner tube configurations modeled above, the parameters available for design are the curvature and arc length of the inner tube 50, such that a given design is defined as d={Lc, r}.

Medical image data, such as CT image data, can be used to evaluate the extent to which an active cannula 30 having a given configuration has a workspace that conforms to or covers a given target. For example, the CT medical image data that is routinely acquired during the diagnosis of an ICH can registered, segmented using software such as 3D Sheer™ (an open-source platform available for download at www.slicer.org). Segmentation can be used to identify the open space between the brain and the skull and also the boundary of the target (ICH). An image model (volume or surface) of the patient's skull, brain and the ICH clot is thereby obtained. The neurosurgeon can then identify on the model the location where the cannula will enter the patient (e.g., the burr hole in the skull) and the location on the ICH clot where the inner tube 50 will enter the clot. The position of the ICH can be mapped relative to the model of the skull.

The joint space of the active cannula 30 ($q=(\rho_1, \rho_2, \alpha)$) can be processed into discrete counterparts and, from this, the workspace of the active cannula 30 can be computed by evaluating or solving the kinematic model for each discrete combination of joint positions. The computed workspace is compared to the image data of the target (e.g., segmented ICH clot image data) to determine the degree to which the two overlap. The degree of overlap is indicative of the extent to which the active cannula 30 having that particular configuration can cover the target. Making this determination requires knowledge of the position and orientation of the target and the accessible trajectories through which the target can be reached. This information is provided by the surgeon, as described above.

In the example implementation, comparing the workspace to the image data of the target determines the extent to which the ICH clot can be evacuated by the active cannula 30 incorporating an inner tube 50 having the configuration evaluated by the kinematic model. In the ICH clot removal implementation, making this determination requires knowledge of the entry point on the patient's skull and the trajectory of the active cannula 30, which are determined by the surgeon as the shortest or otherwise best path along which to reach the target ICH while compromising as little brain structure as possible.

To evaluate the ability of an active cannula 30 having an inner tube 50 with a particular configuration to cover a target of a given shape, a volumetric objective tube selection function was formulated. To formulate this function, the model of the target is converted to a discrete set of isotropic volume elements or "voxels". Voxels inside and outside the target are differentiated using a binary voxel representation. The objective tube selection function for target (e.g., ICH clot) coverage (d) is defined as the percentage of the total clot volume that is accessible by the tip of the active cannula 30 having that particular inner tube 50 configuration.

The portion of the cannula workspace volume that lies within the target V(d) is generated for each d by discretizing the joint space of the active cannula 30 robot and computing the cannula tip position for each combination of joint values. This can be done, for example, with 1 mm translational and 1° rotational increments. A secondary evaluation can be used to determine whether the entire curve of the inner tube 50 is positioned within the target, and joint value combinations in which any portion of the inner tube 50 is positioned outside the clot can be discarded.

For example, to discretize the joint space of the active cannula 30, the inner tube 50 can be advanced 1 mm and, at this translational position, rotated through 360 1° increments, with the position of the tip 32 being calculated at each position. The secondary evaluation of whether the entire curve of the inner tube 50 is positioned within the target can be evaluated at every position. Once all 360 tip positions are evaluated, the inner tube 50 can be advanced another 1 mm increment and the rotational calculations and secondary evaluations repeated.

Each computed cannula tip position is evaluated to determine whether it lies within a voxel of the target model. The voxels that contain tip points are labeled as covered voxels, and those that remain are labeled as uncovered. The percentage of the clot covered can be computed by dividing the total number of target voxels by the number of covered voxels. This process can be repeated with different inner tubes 50 having different tip configurations to determine which tube or combination of tubes provides the ideal target coverage removal percentage. This process can be repeated for various entry points, trajectories, and inner tube configurations of the robot 20. Through this evaluation, the system 10 can be used to determine the ideal inner tube configurations for covering the target. In the example implementation, the system 10 can be used to determine the ideal entry point, trajectory, and combination of inner tube configurations for covering the ICH clot.

Inner Tube Selection Method

From the above, those skilled in the art will appreciate that, according to one aspect, the invention relates to a method for determining the optimal design(s) or configuration(s) for the curved inner tube of a concentric tube active cannula robot. These optimal designs can then be shaped or otherwise manufactured and subsequently used to perform the surgical procedure custom tailored to the target. This method, however, requires the luxury of time, which may not be available depending on the circumstances.

According to another aspect, the invention can also relate to a method for selecting from an existing set of pre-configured tubes a subset of those tubes that provides a workspace for covering a target that is optimal given the circumstances. According to this aspect, a predetermined set of pre-configured inner tubes 50 (e.g., a set of 5, 10 or more tubes) that vary in configuration is made available to the surgeon. Using the kinematic model evaluation approach described above, one or more of the tubes can be selected to provide an active cannula 30 with a workspace that covers the target to the extent possible, given the circumstances. This eliminates the need for time to shape or otherwise manufacture the inner tubes.

According to a further aspect, in a combination of these approaches, the set of pre-configured tubes can be identified through a pre-surgery evaluation in which the kinematic model is evaluated and compared to the image data of the target as described above. Then, during surgery, the kinematic model evaluation can be executed to determine which of the pre-configured tubes to use for the actual procedure. In this manner, the pre-surgery evaluation can take into account factors, such as trajectories, access (burr hole) locations, and even slight changes in clot shape/size, that can vary depending on changing patient conditions or unforeseen complications.

Tube Selection Method

Figure 17A:
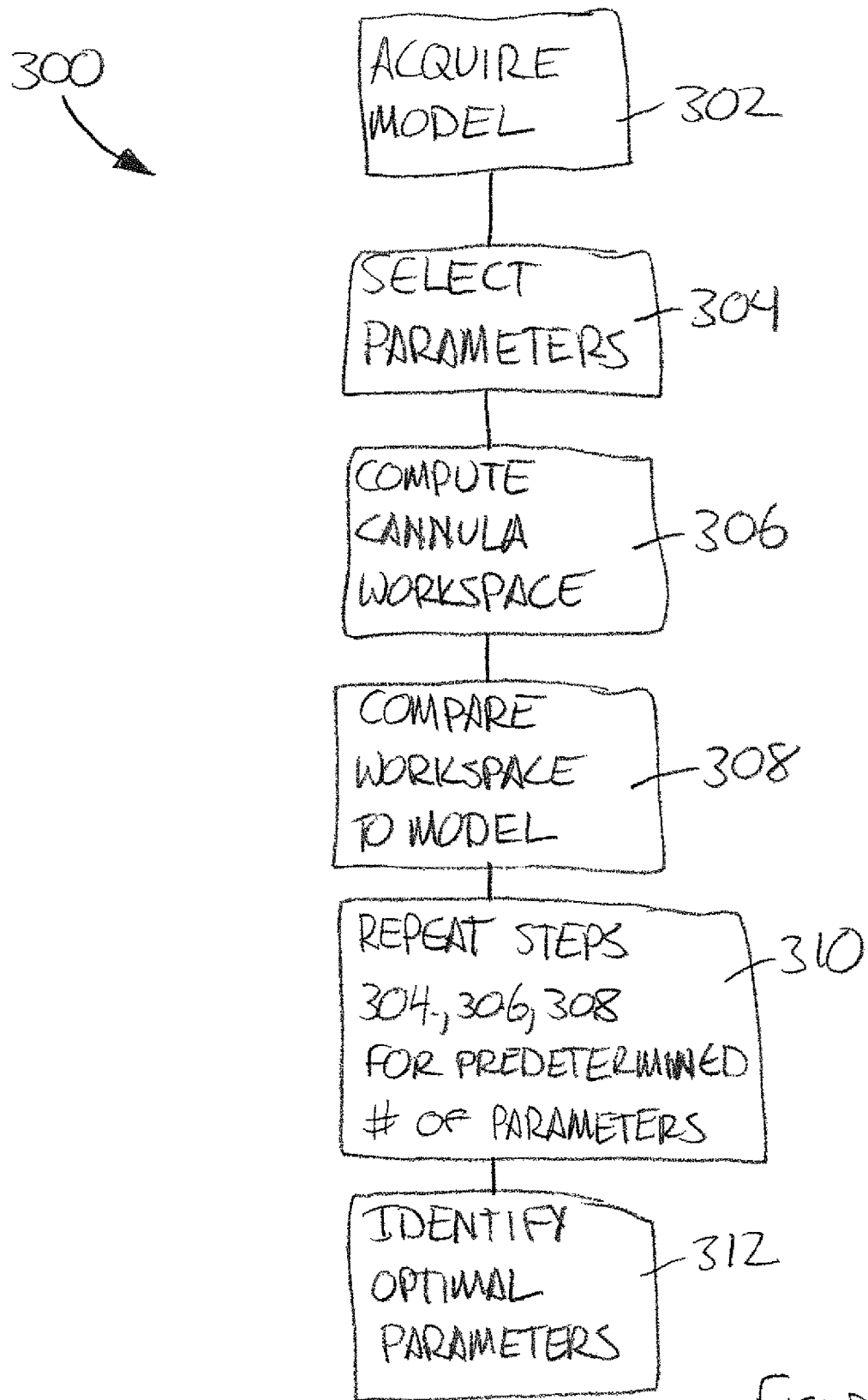
FIGS. 17A-17C illustrate methods according to the invention.
Figure 17B:
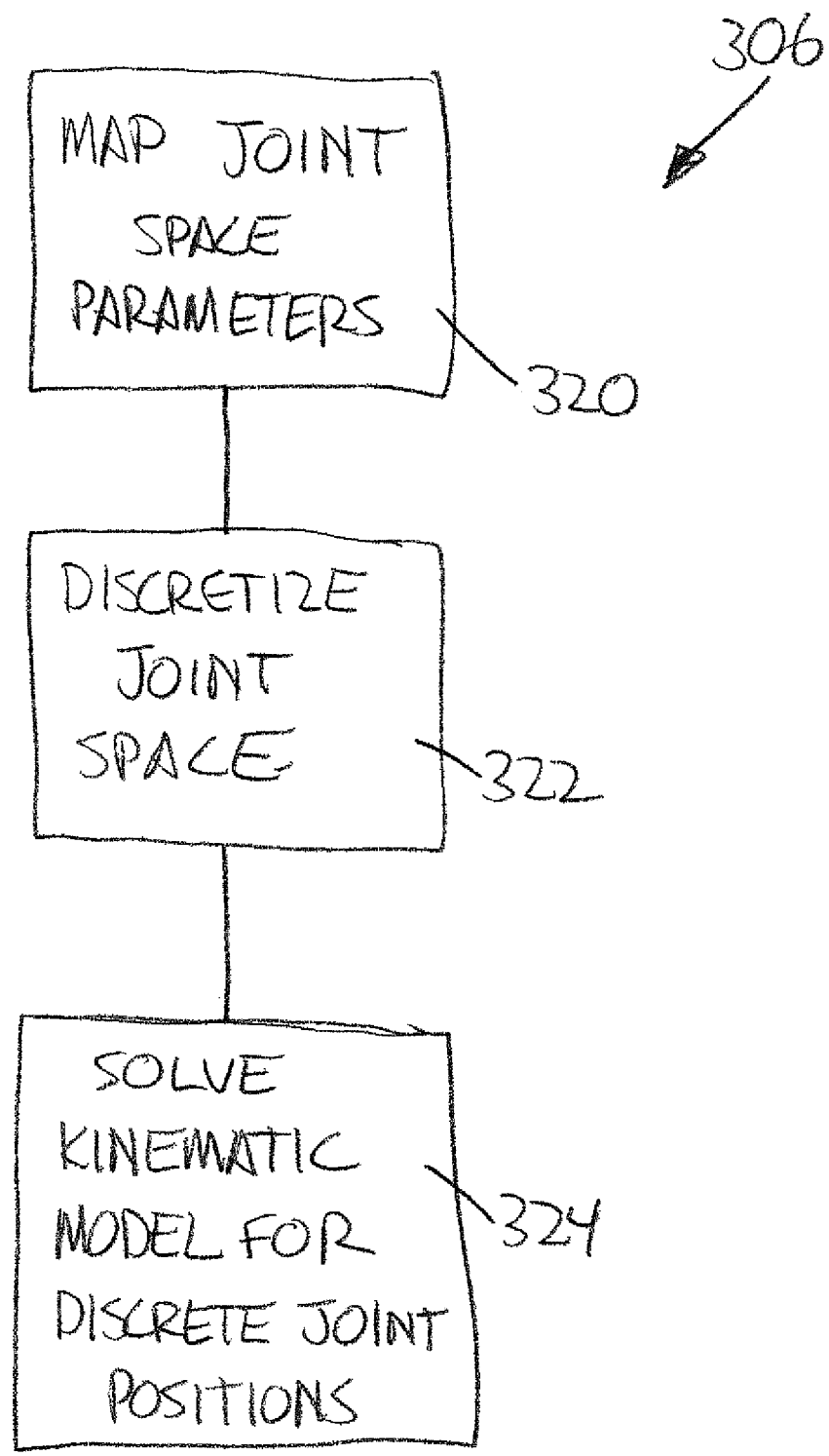
Figure 17C:
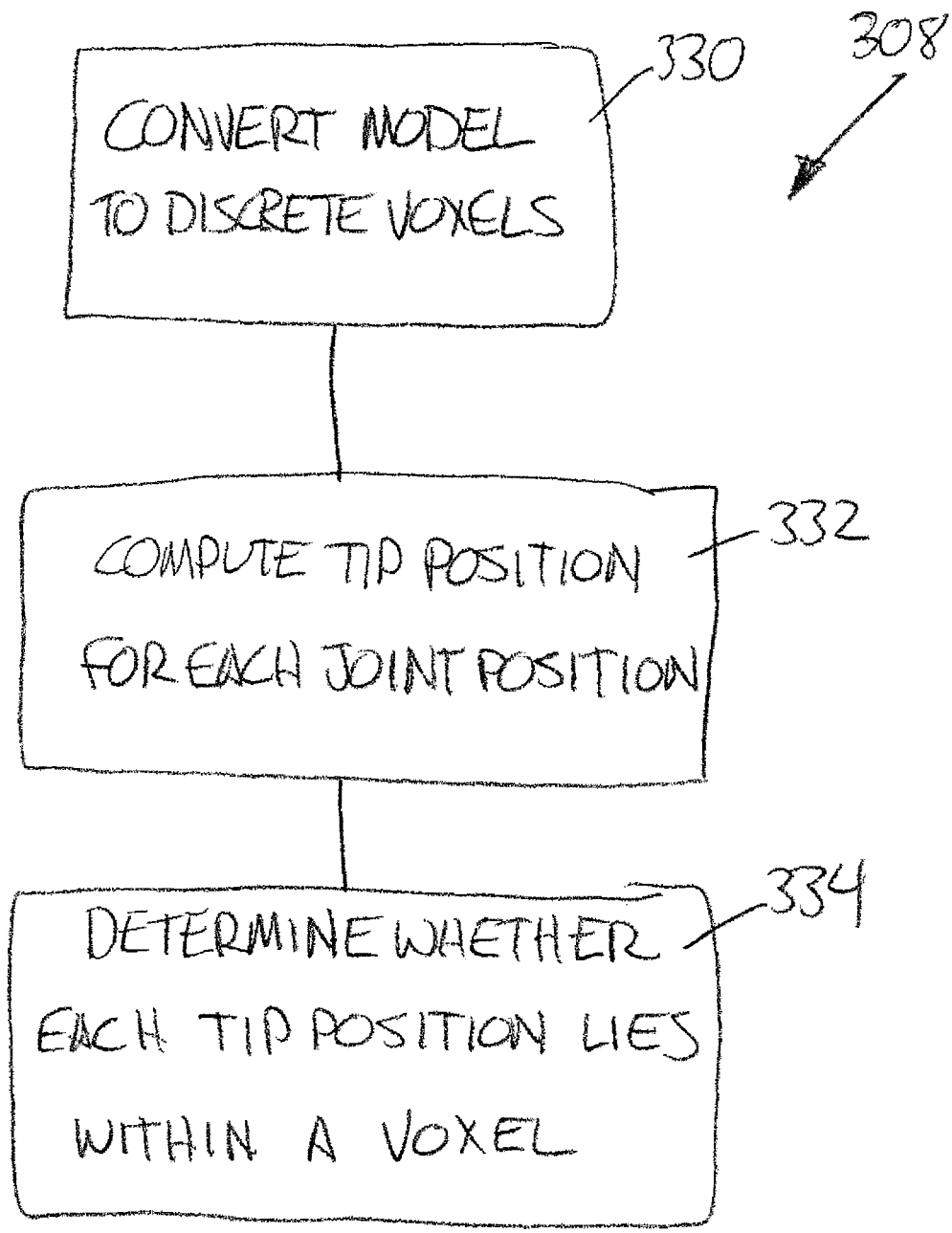

From the above, those skilled in the art will appreciate that the invention relates to a method for identifying tube parameters of a curved tube of an active cannula for operating on a target in a patient. The methods, which can be implemented by the controller 66, including the computer 66*a*, are illustrated in FIGS. 17A-17C. Those skilled in the art will appreciate that the steps illustrated and described herein sequentially, could be performed in different orders or simultaneously.

Referring to FIG. 17A, a method 300 for identifying tube parameters a curved tube of an active cannula for operating on a target in a patient includes the step 302 of acquiring a model of the patient anatomy including the target. The method 300 also includes the step 304 of selecting a set of parameters characterizing a curved tube. The method 300 also includes the step 306 of computing a workspace for an active cannula having the selected curved tube parameters. The method 300 also includes the step 308 of comparing the workspace to the anatomical model to determine the degree to which an active cannula having the selected curved tube parameters can cover the target. The method 300 also includes the step 310 of repeating steps 304, 306, and 308 through a defined number of curved tube parameter sets. The method 300 also includes the further step 312 of identifying the curved tube parameters that provide an active cannula with an optimal degree of target coverage.

FIG. 17B illustrates step 306 of method 300. The step 306 of computing a workspace includes the step 320 of mapping the joint space parameters of the active cannula to configuration space parameters in order to define a forward kinematic model for the active cannula. The step 306 also includes the step 322 of discretizing the joint space of the active cannula to produce a discrete set of joint positions of the active cannula. The step 306 includes the further step 324 of solving the kinematic model for each discrete combination of joint positions to compute the workspace of the active cannula.

FIG. 17C illustrates step 308 of method 300. The step 308 of comparing the computed workspace to the clot model comprises the step 330 of converting the target model to a discrete set of voxels. The step 308 also includes the step 332 of computing a tip position for each of the joint positions of the active cannula. The step 308 includes the further step 334 of evaluating each computed cannula tip position to determine whether it lies within a voxel of the target model.

Demonstrative Examples

To evaluate the effectiveness of the system 10 in the example ICH clot removal implementation, a study was performed utilizing CT datasets from seven patients previously treated for an ICH. For each case, a neurosurgeon selected a desired entry path, and for each path all possible aspiration tube sets were evaluated and calculated using the objective tube selection function described above. Tube parameters used in the objective tube selection function were defined as follows:

- Inner tubes 50 were considered to have an outer diameter of 1.14 mm and an inner diameter of 0.91 mm.
- A 10% recoverable strain threshold was used.
- The curved section length Lc was first discretized in 5 mm steps starting at 10 mm. Then, the same procedure was used with a finer resolution of 2 mm.
- Minimum and maximum radii of curvature were 6.4 and 150 mm, respectively, with 2.5 mm discretization within this range.

For selection of the optimal aspiration tube(s), four scenarios of use were considered. For each scenario, the tables shown below illustrate the optimal tube choice(s) selected by the objective function across both the 5 mm and 2 mm discretizations.

Scenario 1: Single Aspiration Tube

In this first scenario, the active cannula 30 was only permitted to have one inner tube 50, which was required to remain within the clot at all times. For each patient case, the tube curvature and arc length that maximizes coverage of the hematoma (f) was computed as:

$$f^* = \arg \max f(d);$$

with results summarized below in Table 1.

TABLE 1

SUMMARY OF OPTIMAL ASPIRATION TUBES FOR SCENARIO 1

| Case | $l_c$ | R | f* |
|---|---|---|---|
| 1 | 108 | 17.19 | 66% |
| 2 | 85 | 13.53 | 71% |
| 3 | 50 | 10.46 | 85% |

TABLE 1-continued

SUMMARY OF OPTIMAL ASPIRATION TUBES FOR SCENARIO 1

| Case | $l_c$ | R | f* |
|---|---|---|---|
| 4 | 75 | 11.94 | 68% |
| 5 | 70 | 11.14 | 88% |
| 6 | 55 | 13.75 | 61% |
| 7 | 65 | 10.35 | 75% |

For each case, Table 1 shows the ideal configuration for the inner tube 50 given the single tube, remain totally within the clot requirements of Scenario 1. While the single tube level of coverage illustrated in Table 1 exceeds a 25-50% minimum coverage target, two other scenarios of use were considered in order to provide additional options for the neurosurgeon if increased coverage is desired. These scenarios are described and illustrated in the following paragraphs.

Scenario 2: Single Aspiration Tube with Brain Deformation

In this scenario, the requirement that the entire curved tube remains inside the clot at all times was relaxed, instead permitting small lateral deflection of the active cannula tip 32 at the surface of the clot up to some threshold ($t_d$). This is done by positioning the tip of the outer tube 40 outside of and away from the exterior bounds of the ICH clot and then advancing the inner tube 50 so that the tip 32 is permitted to deflect off axis 18 up to threshold $t_d$ prior to entering the clot. By doing this, the volume of clot accessible to a single constant curvature aspiration tube can be increased significantly because the volume of the clot adjacent the outer tube 40 can be evacuated. The results of this scenario are shown below in Table 2.

TABLE 2

SUMMARY OF OPTIMAL ASPIRATION TUBES FOR SCENARIO 2

| Case | $L_c$ | R | $t_d$ | f* |
|---|---|---|---|---|
| 1 | 120 | 19.10 | 14.90 | 93% |
| 2 | 80 | 17.73 | 10.59 | 94% |
| 3 | 110 | 17.51 | 9.09 | 99% |
| 4 | 80 | 12.73 | 3.42 | 88% |
| 5 | 80 | 12.73 | 7.02 | 98% |
| 6 | 60 | 29.63 | 15.00 | 98% |
| 7 | 60 | 44.63 | 15.00 | 100% |

For each case, Table 2 shows the ideal configuration of the inner tube 50 and the allowed deflection outside the ICH clot. Note that, in Scenario 2, the maximum $t_d$ was limited to 15 mm. The amount of permissible $t_d$ is in general based on the preference of the specific surgeon using the system. If $t_d$ is set to zero, then Scenario 2 is identical to Scenario 1. Note also that one could also can achieve a similar result without any deflection outside the ICH clot and therefore without cutting brain tissue by first deploying the inner tube 50 within the clot, and then retracting the outer and inner tubes 40, 50 simultaneously.

Scenario 3: Two Aspiration Tubes in Succession

In this scenario, a configuration of the active cannula 30 was sought that maintains the high coverage achieved in Scenario 2 while eliminating the need for brain deflection ($t_d$). This configuration is achieved by selecting two inner tubes 50 with different curvatures ($d_1$, $d_2$), which will be used sequentially via the hot-swap feature. After the first inner tube 50 has evacuated all of the clot it is able to reach, it is removed with the outer tube 40 remaining in place in the patient's brain so that the system 10 maintains registration. The second inner tube 50 is introduced to remove additional clot material not accessible by the first inner tube. The goal is to choose the parameters of the two tubes simultaneously, such that the overall volume of the clot removed is maximized, as follows:

$$f^* = \arg\max(f(d_1) \cap f(d_2));$$

with the results shown below in Table 3.

TABLE 3

SCENARIO 3: SEQUENTIAL USE OF TWO ASPIRATION TUBES WITH COMBINED COVERAGE $f^*$

| Case | $L_c$ | R | f | $L_c$ | R | f | $f^*$ |
|---|---|---|---|---|---|---|---|
| 1 | 70 | 16.14 | 67% | 60 | 9.55 | 57% | 86% |
| 2 | 60 | 17.05 | 66% | 55 | 8.75 | 62% | 87% |
| 3 | 45 | 12.16 | 82% | 40 | 6.37 | 65% | 94% |
| 4 | 80 | 12.73 | 67% | 45 | 7.16 | 60% | 87% |
| 5 | 60 | 12.05 | 87% | 45 | 7.16 | 60% | 87% |
| 6 | 60 | 14.54 | 60% | 55 | 8.75 | 49% | 78% |
| 7 | 40 | 11.37 | 73% | 40 | 6.36 | 63% | 90% |

For each case, Table 3 shows the best combination of inner tubes 50, their respective coverage percentages, and their combined coverage percentages. The similarity in curvatures of both tubes across all cases is noteworthy, as is the high overall volume of clot removed. To determine how well a single set of two tubes could work across all patients, the optimization was ran again seeking to maximize the average coverage across all patients with a single set of tubes. This resulted in a first tube with $L_c=58$ mm, r=13.23 mm and a second tube with $L_c=40$ mm, r=6.37 mm. This tube set enables an average coverage of 79% across all patients, with a minimum of 60% and a maximum of 95%.

Scenario 4: Discrete Tube Set

This scenario evaluated the performance of a fixed set of five tubes (radii of curvature: 6, 8.5, 11, 13.5, and 16 mm), where the radii were chosen to span the optimal tube curvatures of Scenario 3. A perturbed entry path in which the path deviated from the optimal path was also evaluated. For the optimal path, the five tubes used in sequence were shown to be capable of removing an average of 95%, as shown below in Table 4:

TABLE 4

SCENARIO 4: SEQUENTIAL USE OF FIVE PRESELECTED TUBES AND INFLUENCE OF ENTRY PATH PERTURBATION

| Case | Optimal Entry Path $f^*$ | Perturbed Entry Paths min $f^*$ |
|---|---|---|
| 1 | 92% | 60% |
| 2 | 94% | 85% |
| 3 | 98% | 97% |
| 4 | 96% | 57% |
| 5 | 100% | 95% |
| 6 | 92% | 32% |
| 7 | 95% | 95% |

In the fourth scenario, a perturbation study was performed due to the fact that there can be some uncertainty in burr hole placement and also in targeting the desired clot entry point. In considering the level of error that can be expected in clinical use, it should be noted that the accuracy of the Navigus® components used by the present system 10 to target the ICH location in the brain has been experimentally found to be 1 mm with a standard deviation of 0.28 mm. It should also be noted that the surgeon will have access to image-guidance when selecting the burr hole location and, thus, in principle should be able to place the burr hole at the desired location approximately as accurately as internal skull points can be targeted (i.e., the same image-guidance system is used for both purposes).

A conservative level of error of a little over three standard deviations was introduced with a maximum burr hole error of 2.5 mm and a maximum clot entry point error of 2 mm. The burr hole error was set slightly higher than the clot targeting error to account for the fact that the surgeon may be slightly more careful in internal point targeting than in burr hole placement. The worst case needle angular misalignment within these bounds occurs when both burr hole error and clot entry error simultaneously deviate maximally from the planned locations, and do so in the worst possible direction, i.e., worst with respect both to one another, and with respect to clot geometry. This is a conservative worst case scenario, considering that since the errors are likely Gaussian in nature, it is statistically unlikely that both errors would be maximal simultaneously, let alone in the worst possible direction. Considering this case provides a useful lower bound on worst case scenario clot coverage.

In this scenario, 25 perturbation cases were generated for each of the seven patient cases by considering all combinations of five evenly angularly distributed points at a radial distance of 2.5 mm on the skull surface around a planned burr hole location and five evenly angularly distributed points at a radial distance of 2 mm around the planned clot entry point. Table 4 shows the minimum clot volume coverage across all patient and perturbation cases. It can be concluded from this study that if surgeons are correct in their estimate that decompression benefit begins when 25-50% of the clot is removed, it is statistically improbable that a small number of discrete tubes will be incapable of accessing the requisite geometry.

In Vitro Phantom Material

To further explore the practical feasibility of robot-assisted ICH clot evacuation using a single tube with allowed tissue deflection (see Scenario 2), an experiment was conducted in simulated (sometimes referred to as "phantom") brain material. The inner aspiration tube used had a straight section with Ls=260 mm followed by a section with constant curvature of r=30.3 mm with Lc=55 mm. The aspiration tube had an outer diameter of 1.75 mm and a wall thickness of 0.3 mm. The outer tube had an outer diameter of 3.2 mm and a wall thickness of 1 mm.

The experiment was conducted using gelatin as both a simulated brain tissue and ICH clot. In this experiment, simulated brain tissue was made using 10% by weight clear Knox gelatin (available commercially from Kraft Foods Global, Inc., USA), and the simulated clot was made with red Jell-O gelatin. The simulated clot was softer than the simulated brain tissue. The simulated ICH was approximately spherical with a 63.5 mm diameter.

The trajectory stem 170 was aligned with the clot and secured using the locking ring 174. The robot 20 was then affixed to the passive arm 22 and attached to the trajectory stem 170. The active cannula 30 was then inserted into the clot, with the inner tube 50 retracted fully inside the outer tube 40, and the tubes were then used to evacuate the clot. Motion planning was conducted manually by the experimenter who visually observed the debulking process through the wall of the phantom brain tissue and input new desired target locations to the robot manually using the computer keyboard. The robot 20 was able to remove 92% of the clot material, determined by initially measuring the amount of red gelatin used. The surface of the clot was visually inspected for positive margins and none were detected. The residual simulated clot material left after the end of the experiment was collected and weighed. The achieved results are similar to the 99% theoretical coverage of this clot discussed above in regard to Scenario 2. The system 10 could have removed more of the simulated clot material at the clot-brain interface if there had been less concern with damaging the simulated healthy brain tissue. This could have been done, for example, by increasing the allowable $t_d$ (see Table 2).

In Vitro Skull Experiment

An in vitro experiment was performed using an anatomically correct skull model to experimentally demonstrate the system 10 under conditions similar to those in patient case 1 of Scenario 3. To replicate the geometry of patient case 1, a two-piece semi-transparent plastic skull which was filled with gelatin to simulate brain tissue. A gelatin model of the segmented clot from patient case 1 was suspended in the brain tissue gelatin at a position and orientation similar to that of patient case 1. Barium was added to the clot gelatin to enable visualization of the clot in the CT image.

The nitinol inner tubes 50 used in this experiment were modeled after those listed in Table 3 for patient case 1, although the tubes relaxed slightly as they were removed from the heat treatment fixture, so the resulting radii of curvature were 19.8 mm and 12.6 mm. The robot 20 was aligned with the entry path selected by an experienced neurosurgeon, in a manner similar or identical to those discussed previously. Because the skull was not completely transparent, the top of the skull was removed after the robot was aligned to enable visualization of the tubes in the clot. Motion planning, robot position commands, and determination of the removed clot volume were implemented in the same or a similar manner to that described above in the in vitro phantom experiment.

The robot 20 was able to remove 83.1% of the clot, measured in a manner identical to the manner described above in the in vitro phantom experiment. Based on the curvatures of the experimental tubes, the expected clot removal percentage was 80.6% (using the actual 19.8 mm and 12.6 mm radii). The fact that the experimental results slightly exceeded the theoretical prediction can be attributed to minor tissue deformation as suction was applied, which brings more material within reach of the cannula tip. Note that deformation also is likely to be present in human brain tissue, so the theoretical percentages described herein (which consider only rigid geometry) may be conservative.

Robot Operation and Control—Evacuating the ICH Clot

Having determined the optimal configuration for the inner tube or tubes 50 for evacuating a particular ICH clot in accordance with the methods described above, the system 10 can be operated to remove an ICH clot. Because the inner tube(s) 50 are selected based on CT image data of the ICH clot, and because the active cannula robot 20 is registered for surgery using the image guidance system 38, the workspace of the active cannula 30 will coincide with the shape, location, and orientation of the clot. The clot can therefore be evacuated by applying suction to the inner tube 50 and moving the tip 32 of the tube systematically through the workspace. To accomplish this, the robot 20 can be operated manually by the surgeon with real time monitoring via the image guidance system 38 or automatically by the controller 66.

Manual operation can be performed in a pure manual mode (described below) or teleoperatively. To perform the surgery in a teleoperative manual mode, the surgeon uses the controller 66 to command low level movements of the robot. Through this teleoperative manual control, the surgeon inserts the active cannula 30 with the inner tube 50 retracted so that the outer (needle) tube 40 can enter the brain via the trajectory guide 170 to reach the ICH location. At the ICH location, the surgeon can operate the active cannula 30 via controller commands to progressively insert and rotate the inner tube 50 in the clot while applying suction to evacuate the clot, while monitoring the image guidance system to maintain the tip 32 within the clot.

Figure 16B:
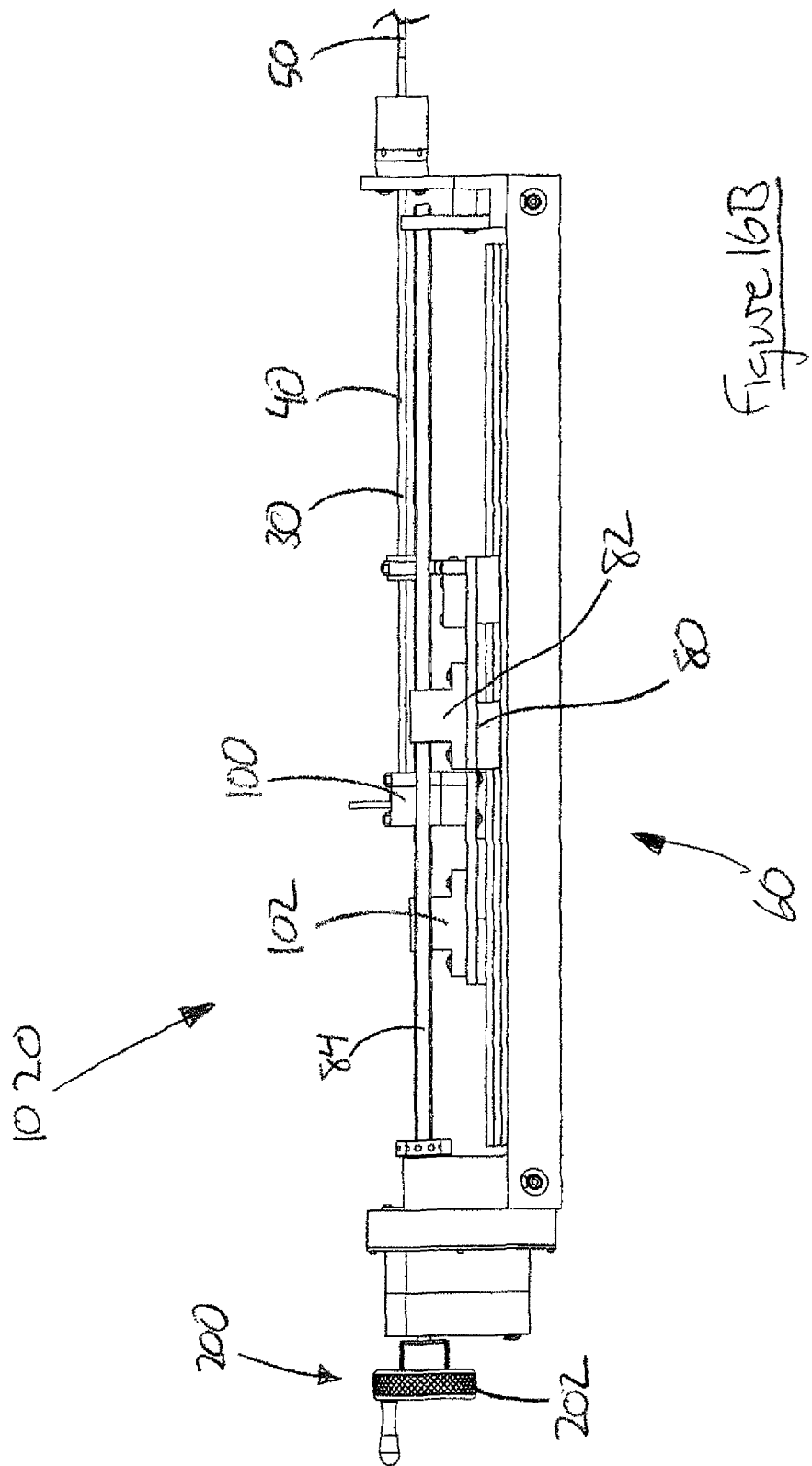

In a pure manual mode, the motor pack is replaced with manual controls 200 as shown in FIGS. 16A and 16B. The controls 200 include manual actuators in the form of wheels 202 and 204 that are linked to the shafts 84, 104, respectively and are thereby rotatable to cause insertion and retraction of the outer tube 40 and inner tube 50, respectively. The controls 200 also include a manual actuator in the form of a knob 206 that is linked to the shaft 120 and is thereby rotatable to cause rotation of the inner tube 50 about the axis 18.

To perform the surgery in the pure manual mode, the surgeon uses the manual controls 200 to command movements of the active cannula 30. Through manual manipulation of the wheels 202, 204, the surgeon inserts the active cannula 30 with the inner tube 50 retracted so that the outer (needle) tube 40 can enter the brain via the trajectory guide 170 to reach the ICH location. At the ICH location, the surgeon can operate the active cannula 30 via the manual controls 200 to progressively insert (wheel 204) and rotate (knob 206) the inner tube 50 in the clot while applying suction to evacuate the clot, while monitoring the image guidance system to maintain the tip 32 within the clot.

The robot 20 can also perform the surgery automatically under open loop control in which the controller 66 operates the robot to actuate the cannula 30 according to instructions "learned" by the controller during the execution of the objective tube selection function. Since the execution of this function necessarily determines which of the discretized positions of the inner tube(s) 50 fall inside the clot and which fall outside the clot, these determinations can serve as a guide or map for operating the robot 20 in an open loop control scheme to automatically evacuate the ICH. Such automatic control can, of course, be monitored in real time by the surgeon via the image guidance system 38. This open loop automatic robot control can also be broken down into steps or increments that the surgeon can initiate manually, one step at a time, to evacuate the ICH clot.

The foregoing has described a system, method, and apparatus for image guided evacuation of a hematoma resulting from an intracerebral hemorrhage using a robotic active cannula. While specific embodiments of the invention have been described, it will be apparent to those skilled in the art that various modifications thereto can be made without departing from the spirit and scope of the invention. For example, while the embodiments described herein have related to an active cannula configuration with a single curved tube, those skilled in the art will appreciate that some or all of these features are applicable to multi-curved tube configurations. Accordingly, the foregoing description of the invention is provided for the purpose of illustration only and not for the purpose of limitation.

We claim:

1. An active cannula robot for performing a surgical operation on a patient, the robot comprising:
   an actuation unit;
   an inner cannula tube positioned concentrically within an outer cannula tube, the outer cannula tube having a straight configuration, the inner cannula tube comprising a curved end portion that is retractable into the outer cannula tube, the curved end portion deforming elastically and conforming to the straight configuration of the outer cannula tube when retracted into the outer cannula tube and returning resiliently to its curved configuration when extended from the outer cannula tube;

a transmission tube assembly comprising an inner transmission tube positioned concentrically within an outer transmission tube, the outer transmission tube being coupled to the actuation unit and coupled directly to the outer cannula tube, the inner transmission tube being coupled to the actuation unit and coupled directly to the inner cannula tube, wherein the actuation unit is actuatable to cause extension and retraction of the outer transmission tube along an axis, and wherein the actuation unit is actuatable to cause extension of the inner transmission tube relative to the outer transmission tube along the axis, retraction of the inner transmission tube relative to the outer transmission tube along the axis, and rotation of the of the inner transmission tube relative to the outer transmission tube about the axis;

wherein the outer cannula tube extends and retracts along the axis with the outer transmission tube, the inner cannula tube extends and retracts along the axis with the inner transmission tube, and the inner cannula tube rotates about the axis with the inner transmission tube;

wherein the inner and outer transmission tubes have torsional stiffnesses that are greater than torsional stiffnesses of the inner and outer cannula tubes.

2. The robot recited in claim 1, wherein the actuation unit comprises:

a frame having a front end and an opposite rear end;

an outer tube carrier coupled to the frame, the outer tube carrier being movable along the frame to cause the translational movement of the outer transmission tube along the axis;

an inner tube carrier coupled to the frame, the inner tube carrier being movable along the frame to cause translational movement of the inner transmission tube along the axis, the inner tube carrier comprising a tube mount for supporting the inner transmission tube for rotation about the axis, a retainer for securing the inner transmission tube in the tube mount, the retainer being manually releasable to permit removal of the inner transmission tube and inner cannula tube and replacement with a different inner transmission tube and inner cannula tube during a surgical operation without retracting the outer transmission tube and outer cannula tube; and a motor assembly coupled to the rear end of the frame, the motor assembly comprising a first motor operable to move the outer tube carrier along the frame, a second motor operable to move the inner tube carrier along the frame, and a third motor operable to impart rotation of the inner transmission tube about the axis.

3. The robot recited in claim 2, further comprising a trajectory stem that is decoupled from the actuation unit and is configured to be secured to the patient, wherein the front end of the frame is configured to be received by the trajectory stem so that the trajectory stem guides the trajectory of the outer cannula tube when extended from the frame into a patient.

4. The robot recited in claim 2, wherein the retainer permits removal and replacement of the inner transmission tube without disturbing the remaining components of the robot.

5. The robot recited in claim 2, wherein the outer tube carrier comprises emergency release mechanisms that are manually operable to decouple the outer tube carrier from the first motor and to decouple the inner tube carrier from the second motor to permit the tube carriers to be moved manually along the frame in order to retract the inner and outer cannula tubes.

6. The robot recited in claim 2, wherein:

the outer tube carrier comprises a driver block through which a shaft rotatable by the first motor extends, rotation of the shaft acting on the driver block to impart movement of the outer tube carrier along the frame, the driver block comprising an emergency release mechanism that is manually operable to decouple the driver block from the outer tube carrier and thereby decouple the outer tube carrier from the first motor; and the inner tube carrier comprises a driver block through which a shaft rotatable by the second motor extends, rotation of the shaft acting on the driver block to impart movement of the inner tube carrier along the frame, the driver block comprising an emergency release mechanism that is manually operable to decouple the driver block from the inner tube carrier and thereby decouple the inner tube carrier from the second motor.

7. The robot recited in claim 2, wherein the motors of the motor assembly are operable to actuate the inner and outer transmission tubes to actuate the inner and outer cannula tubes in order to perform a surgical operation to evacuate a clot resulting from an intracerebral hemorrhage through the inner cannula tube.

8. The robot recited in claim 7, wherein the first motor is operable to deliver the outer cannula tube to the clot in an axial direction with the inner cannula tube retracted into the outer cannula tube, the second motor being operable to extend the curved end portion of the inner cannula tube from the outer cannula tube into the clot to evacuate the clot.

9. The robot recited in claim 7, wherein the second and third motors are operable to translate and rotate the curved end portion of the inner cannula tube within the clot to evacuate the clot.

10. The robot recited in claim 7, wherein the second and third motors are operable to move the position of a distal tip of the inner tube through a predetermined path within the clot to evacuate the clot.

11. The robot recited in claim 7, further comprising an aspirator operatively connected to the inner cannula tube, the aspirator being operable to apply suction via the inner cannula tube to evacuate the clot.

12. The robot recited in claim 2, further comprising a second retainer for securing the outer transmission tube to the robot, the second retainer being manually releasable to permit removal and replacement of the outer transmission tube and the outer cannula tube during the surgical operation.

13. The robot recited in claim 2, further comprising a second retainer for securing the outer transmission tube to the robot, the second retainer being manually releasable to permit removal and replacement of the outer transmission tube and the outer cannula tube without disturbing the remaining components of the robot.

14. The robot recited in claim 2, wherein the inner tube carrier and outer tube carrier are configured to be independently operable to cause the translational movement of the inner cannula tube along the axis, the rotational movement of the inner cannula tube about the axis, and the translational movement of the outer cannula tube along the axis independently of each other.

15. The robot recited in claim 1, further comprising a trajectory stem for guiding the outer cannula tube along a predetermined trajectory, the trajectory stem being decoupled from the actuation unit, wherein the trajectory stem is configured to force the outer cannula tube to follow the predetermined trajectory.

16. The robot recited in claim 15, further comprising a base coupled to the trajectory stem and comprising a locking mechanism for fixing the position of the trajectory stem at a desired orientation relative to the patient and relative to the axis, the base being connectable to a patient.

17. The robot recited in claim 1, wherein the robot further comprises:
    a frame having a front end and an opposite rear end;
    an outer tube carrier coupled to the frame, the outer tube carrier being movable along the frame to cause the translational movement of the outer transmission tube and outer cannula tube along the axis;
    an inner tube carrier coupled to the frame, the inner tube carrier being movable along the frame to cause translational movement of the inner transmission tube and the inner cannula tube along the axis, the inner tube carrier comprising a tube mount for supporting the inner transmission tube and inner cannula tube for rotation about the axis, the retainer for securing the inner transmission tube and inner cannula tube in the tube mount; and
    a manual actuator coupled to the rear end of the frame, the manual actuator comprising a first manual actuator operable to move the outer tube carrier along the frame, a second manual actuator operable to move the inner tube carrier along the frame, and a third manual actuator operable to impart rotation of the inner cannula tube about the axis.

\* \* \* \* \*